(12) United States Patent
Sinton et al.

(10) Patent No.: US 10,001,435 B1
(45) Date of Patent: Jun. 19, 2018

(54) METHODS AND APPARATUSES FOR MEASURING MATERIAL PHASE PROPERTIES

(71) Applicant: The Governing Council of the University of Toronto, Toronto (CA)

(72) Inventors: David Sinton, Toronto (CA); Jason Riordon, Toronto (CA); Yi Xu, Toronto (CA); Bo Bao, Edmonton (CA)

(73) Assignee: The Governing Council of the University of Toronto, Toronto, Ontario (CA)

( * ) Notice: Subject to any disclaimer, the term of this patent is extended or adjusted under 35 U.S.C. 154(b) by 0 days. days.

(21) Appl. No.: 15/482,000

(22) Filed: Apr. 7, 2017

(51) Int. Cl.
| | |
|---|---|
| G01N 15/14 | (2006.01) |
| B01L 3/00 | (2006.01) |
| G01N 1/40 | (2006.01) |
| G01R 33/12 | (2006.01) |
| G01N 3/32 | (2006.01) |

(52) U.S. Cl.
CPC ...... G01N 15/1484 (2013.01); B01L 3/50273 (2013.01); B01L 3/502784 (2013.01); G01N 1/4022 (2013.01); G01N 3/32 (2013.01); G01N 15/1463 (2013.01); G01R 33/12 (2013.01); B01L 2300/14 (2013.01); B01L 2400/0487 (2013.01)

(58) Field of Classification Search
CPC .... G01N 15/1484; G01N 1/4022; G01N 3/32; G01N 15/1463; B01L 3/50273; B01L 3/502784; G01R 33/12
See application file for complete search history.

(56) References Cited

U.S. PATENT DOCUMENTS

| | | | |
|---|---|---|---|
| 4,395,902 A | 8/1983 | Espenscheid et al. | |
| 6,223,588 B1 | 5/2001 | Burgass et al. | |
| RE38,129 E | 6/2003 | Kleinberg | |
| 8,340,913 B2 | 12/2012 | Mostowfi et al. | |
| 8,380,446 B2 | 2/2013 | Mostowfi et al. | |
| 8,797,517 B2 | 8/2014 | Karnes et al. | |
| 2005/0266582 A1 * | 12/2005 | Modlin ................ | B01L 3/5027 436/164 |
| 2012/0190127 A1 | 7/2012 | Fraden | |

FOREIGN PATENT DOCUMENTS

WO 2014158376 A1 10/2014

* cited by examiner

*Primary Examiner* — Jennifer Wecker
(74) *Attorney, Agent, or Firm* — Norton Rose Fullbright Canada LLP

(57) ABSTRACT

Methods and apparatuses for determining a material characteristic of a sample material are disclosed. A sample material is loaded to a plurality of cells. An interference material is disposed relative to the sample material such that the interference material at least retards the transport of the sample material from a one of the cells to at least another one of the cells. For each one of the cells, independently: a stimulus is applied to the sample material in the cell such that a conditioned sample material is obtained; and a material characteristic of the conditioned sample material is sensed.

20 Claims, 9 Drawing Sheets

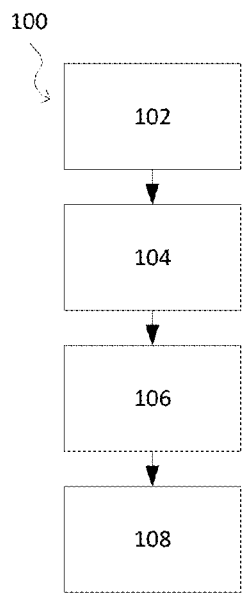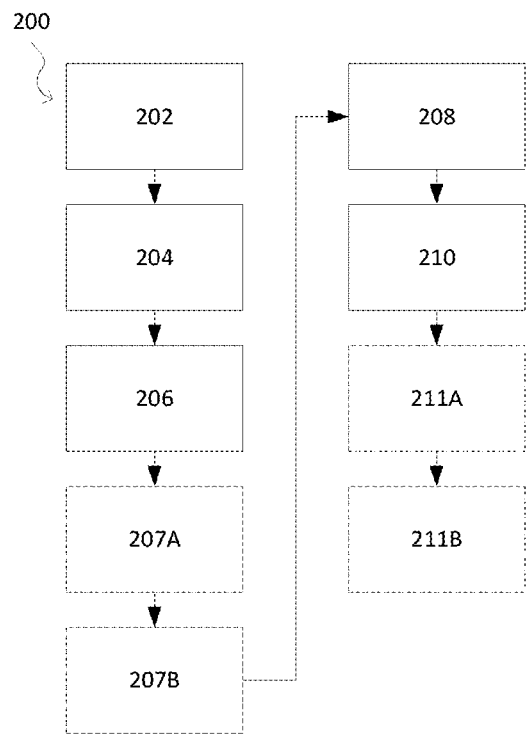
Fig 1
Fig 2
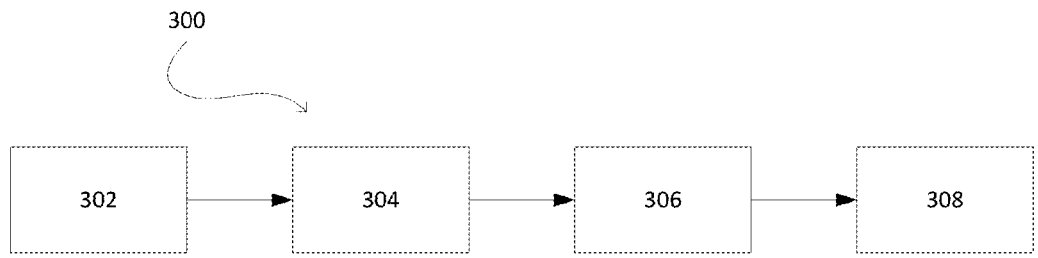
Fig 3

METHODS AND APPARATUSES FOR MEASURING MATERIAL PHASE PROPERTIES

FIELD

This invention relates to methods and apparatuses for analyzing properties of a sample material. More particularly, the invention relates to methods and apparatuses for analyzing phase properties of a sample material.

BACKGROUND

Phase behaviour properties for a material have varied uses. These properties may be taken into consideration when designing or operating chemical or physical processes involving the material.

One potential use of the phase behaviour properties of a material is in the extraction of hydrocarbons from an underground reservoir. When the phase behaviour properties of a reservoir material disposed within the underground reservoir are better understood, operating the extraction can be made safer, and the recovery of the reservoir material can be optimized. Likewise the phase behaviour properties of any injected fluid, under a range of conditions, are relevant to many oil and gas operations.

Another potential use of the phase behaviour properties of a material is in addressing $CO_2$ emissions. Climate change may be influenced by factors including anthropogenic $CO_2$ emissions. Capture, conversion or storage of $CO_2$ will require safe transport of $CO_2$ via pipelines. Industrial $CO_2$ is often mixed with other compounds. The phase properties of the mixture are dependent on the amounts of each compound present in the mixture. Often, small changes in the composition can have large effects on the phase behavior properties. The determination of the phase behaviour properties of a specific $CO_2$ mixture, or other mixture, can help determine conditions for safe transport in pipelines. If a gaseous mixture comprising $CO_2$ and water vapour were transported in a pipe, it may be desirable to design and operate the transport line at conditions where no liquid phase would form. If water were to condense in the pipe, the reaction with the $CO_2$ may generate corrosive acids. Further, sequestration operations may require that the $CO_2$ is safely stored and disposed of at particular conditions, such as disposal by dissolving it in a saline aquifer. The conditions at which these aquifers are present can affect whether it is safe to dissolve and store the sequestered $CO_2$ in such aquifers.

A major limitation of traditional phase property measurement technologies is that only a single pressure-temperature condition can be measured at one time. The most common configuration is the pressure-volume-temperature (PVT) cell, common in petro-chemical and polymer processing applications. These cells typically vary in size between 100 mL and 1 L, and reach pressures and temperatures of 60 MPa and 150° C., respectively. Since thermal and chemical equilibrium within these large systems must be reached between measurements, obtaining a full map of fluid phase behavior can take months, at considerable expense.

Microfluidic technologies have emerged as a tool for rapid, parallel measurements, leveraging short micro-scale diffusion times. U.S. Pat. No. 8,340,913 describes microfluidic techniques that measure pressure-temperature phase properties within a single microchannel including dew point and bubble point. However, phase mapping within a continuous flow suffers drawbacks such as from poor precision due to multiphase flow instabilities, high-speed imaging limitations, subjective operator assessment, and impurity accumulation at phase change interfaces.

There exists a need for improved methods and apparatuses for determining phase properties of a sample fluid.

SUMMARY

In one aspect, there is provided a method for determining a material characteristic of a sample material comprising: loading a sample material to a plurality of cells; disposing an interference material relative to the sample material such that the interference material at least retards the transport of the sample material from a one of the cells to at least another one of the cells; and for each one of the cells, independently: applying a stimulus to the sample material in the cell such that a conditioned sample material is obtained; and sensing a material characteristic of the conditioned sample material.

In some embodiments, the sample material is immiscible or substantially immiscible relative to the interference material. In some embodiments, for each one of the cells, independently, a contact angle between the interference material and the cell is lower than a contact angle between the sample material and the cell. In some embodiments, the interference material is chemically inert with respect to the sample material. In some embodiments, the interference material comprises a fluid. In some embodiments, the fluid is a liquid, gas, or plasma. In some embodiments, the fluid is a liquid. In some embodiments, the liquid is liquid metal, glycerol, ethylene glycol, oil, or any mixture thereof. In some embodiments, the interference material has a viscosity of 0.1-100 cP. In some embodiments, the interference material has a surface tension of from 0.01-10 N/m.

In some embodiments, the applying the stimulus modulates pressure, temperature, voltage, radiation dose, electric field, magnetic field, or a combination thereof of the sample material in the cell.

In some embodiments, the applying the stimulus modulates the pressure of the sample material in the cell. In some embodiments, the applying the stimulus comprises pressurizing the interference material, wherein the interference material communicates pressure to the cell thereby modulating the pressure of the sample material in the cell.

In some embodiments, the applying the stimulus modulates the temperature of the sample material in the cell. In some embodiments, the applying the stimulus comprises modulating the temperature of the sample material in the cell by a Peltier, a heat exchanger, a heating element, a laser heater, an optical heater, or combination thereof. In some embodiments, the temperature is modulated by a heat exchanger. In some embodiments, at least a portion of the heat exchanger is integral with at least a portion of the cell. In some embodiments, the integral portion comprises metal, glass, plastic, or a combination thereof. In some embodiments, the integral portion comprises silicon.

In some embodiments, the plurality of cells comprises a plurality of rows and a plurality of columns, the stimulus modulates a first material property selected from pressure, temperature, voltage, radiation dose, electric field, and magnetic field parameter such that the first material property is substantially constant in cells of a row of the plurality of rows, and wherein the stimulus modulates a second material property selected from pressure, temperature, voltage, radiation dose, electric field, and magnetic field parameter such that the second material property is substantially constant in cells of a column of the plurality of columns.

In some embodiments, the sensing is performed through an electromagnetic radiation transmissive portion of the cell.

In some embodiments, the sensing comprises optical sensing, fluorescence sensing, Raman spectroscopy, conductivity sensing, or any combination thereof.

In some embodiments, each one of the cells, independently, has an internal surface area to volume ratio of between $1\times10^{-6}$ nm$^{-1}$ and 1 nm$^{-1}$. In some embodiments, each one of the cells, independently, has an internal surface area to volume ratio of about 0.154 nm$^{-1}$. In some embodiments, the cells have a height of at most 1 mm. In some embodiments, the height of each cell is between 5 nm and 200 µm. In some embodiments, the height of each cell is between 10 nm and 100 µm. In some embodiments, the cells are microfluidic cells. In some embodiments, the cells have a height of between 10 µm and 100 µm. In some embodiments, the cells are nanofluidic cells. In some embodiments, the cells comprise a height of less than 100 nm. In some embodiments, the width of each cell is between 5 nm and 200 µm. In some embodiments, the width of each cell is between 10 nm and 100 µm. In some embodiments, the cells comprise a width of between 5 µm and 100 µm.

In some embodiments, the pressure of the conditioned sample material is between 0 MPa and 20 MPa. In some embodiments, the pressure of the conditioned sample material is between 0 MPa and 8 MPa.

In some embodiments, the temperature of the conditioned sample material is between –10° C. and 500° C. In some embodiments, the temperature of the conditioned sample material is between –10° C. and 200° C.

In some embodiments, the material characteristic comprises a state of matter, a volume ratio between phases of the conditioned sample material within a cell, a refractive index, an absorbance spectra, a conductivity, or a combination thereof.

In some embodiments, the sample material comprises an oil reservoir fluid, a biological fluid, a biomedical fluid, an environmental fluid, or a combination thereof. In some embodiments, the sample material comprises a mixture of hydrocarbon molecules.

In some embodiments, the transport being retarded includes transport across an interface between the sample material and the interference material.

In some embodiments, the method further comprises determining a critical point, a dew point, a bubble point, a melting point, a boiling point, a eutectic point, a cricondentherm, a cricondenbar, quality lines, or a combination thereof using the sensed material characteristic.

In some embodiments, the method further comprises generating a phase diagram using the sensed material characteristics.

In some embodiments, a device comprises the plurality of cells, wherein the device comprises a sensory layer and an etched layer bonded to the sensory layer, such that the volumes of the cells are defined by the sensory layer and the etched layer.

In one aspect, there is provided method for determining a material characteristic of a material comprising: flowing a material through a main channel such that a first pressure is established and is communicated to a branch channel from the main channel; applying a first stimulus to material within a first space of the branch channel for modulating a material property parameter of the material within the first space of the branch channel; applying a second stimulus to material within a second space of the branch channel for modulating a material property parameter of the material within the second space of the branch channel; sensing a material characteristic of the material within the first space of the branch channel; and sensing a material characteristic of the material within the second space of the branch channel.

In some embodiments, the material property parameter of the material within the first space of the branch channel, and the material property parameter of the material within the second space of the branch channel are, independently, temperature. In some embodiments, the first stimulus and the second stimulus are, independently, applied by a Peltier, a heat exchanger, a heating element, a laser heater, an optical heater, or combination thereof. In some embodiments, the first stimulus and the second stimulus are, independently, applied by a heat exchanger. In some embodiments, the heat exchanger applying the first stimulus and the heat exchanger applying the second stimulus are different portions of the same heat exchanger. In some embodiments, at least a portion of the heat exchanger is integral with at least a portion of the first space. In some embodiments, the at least a portion of the heat exchanger comprises silicon.

In some embodiments, the flowing of the material through the main channel establishes a second pressure downstream from the first pressure, and wherein the second pressure is communicated to a downstream branch channel, the downstream branch channel connecting to the main channel downstream of the branch channel; wherein the method further comprises: applying a third stimulus to material within a first space of the downstream branch channel for modulating a material property parameter of the material within the first space of the downstream branch channel; applying a fourth stimulus to material within a second space of the downstream branch channel for modulating a material property parameter of the material within the second space of the downstream branch channel; sensing a material characteristic of the material within the first space of the downstream branch channel; and sensing a material characteristic of the material within the second space of the downstream branch channel.

In some embodiments, the branch channel and the downstream branch channel are substantially parallel, wherein the distance from the connection point of the main channel and the branch channel to the first space of the branch channel is about equal to the distance from the connection point of the main channel and the downstream branch channel to the first space of the downstream branch channel, and wherein the modulated material property of the material within the first space of the branch channel is modulated to a substantially equal condition to the modulated material property of the material within the first space of the downstream branch channel.

In some embodiments, the branch channel comprises a first cell and a second cell, the first space of the branch channel being defined by the first cell, the second space of the branch channel being defined by the second cell, wherein the material within the first space of the branch channel is a first sample fluid, and the material within the second space of the branch channel is a second sample fluid; and wherein the flowed material is an interference material that at least retards the transport of the first sample fluid from the first space of the branch channel to the second space of the branch channel, and at least retards the transport of the second sample fluid from the second space of the branch channel to the first space of the branch channel.

In some embodiments, the method further comprises generating a phase diagram using the sensed material characteristics.

In one aspect, there is provided a method for determining a material characteristic of a material comprising: flowing a material through a main channel such that a first pressure is established and is communicated to a branch channel from the main channel, wherein the branch channel comprises a first space and a second space; applying a first stimulus to only material within the first space of the branch channel for modulating a material property parameter of the material within the first space of the branch channel; sensing a material characteristic of the material within the first space of the branch channel; and sensing the material characteristic of material within the second space of the branch channel.

In some embodiments, the method further comprises: applying a second stimulus to the material within the second space of the branch channel for modulating a material property parameter of the material within the second space of the branch channel.

In one aspect, there is provided an apparatus for determining phase properties of a sample material comprising: a fluid device comprising: a plurality of cells; a channel connected to the plurality of cells, the channel configured receive a flow of an interference material such that the interference material at least retards the transport of a sample material disposed one of the cells to another of the cells; a stimulator configured to apply an individual stimulus to each one of the cells to condition sample material disposed therein; and a sensor configured to sense a material characteristic of material within each one of the cells.

In some embodiments, the stimulator comprises a pressure modulator for modulating the pressure of material within each one of the cells. In some embodiments, the stimulator comprises a pump for pressurizing the interference material.

In some embodiments, the channel comprises a main channel and at least one branch channel connected to the main channel configured such that, when the interference material is pumped through the main channel, the pressure in each branch channel, independently, is substantially the same. In some embodiments, the at least one branch channel is a plurality of branch channels.

In some embodiments, the device comprises an sensory layer and an etched layer, wherein the volumes of the channel and the volumes of the plurality of walls are defined by void space between the sensory layer and the etched layer. In some embodiments, the stimulator comprises a temperature modulator for modulating the temperature of the sample material within each cell of the plurality of cells. In some embodiments, the temperature modulator is a Peltier, a heat exchanger, a heating element, a laser heater, an optical heater, or a combination thereof. In some embodiments, a front side of the etched layer comprises at least a portion of each cell of the plurality of cells and a rear side of the etched layer comprises at least a portion of the heat exchanger such that the at least a portion of each cell of the plurality of cells is integral with the at least a portion of the heat exchanger.

In some embodiments, the sensor comprises an optical sensor, a spectrometer, a fluorometer, a Raman microscope, a refractometer, or any combination thereof. In some embodiments, the cells have a height of at most 1 mm. In some embodiments, the height of each cell is between 5 nm and 200 µm. In some embodiments, the height of each cell is between 10 nm and 100 µm. In some embodiments, the device is a microfluidic device. In some embodiments, the cells have a height of between 10 µm and 100 µm. In some embodiments, the device is a nanofluidic device. In some embodiments, the cells have a height of less than 100 nm.

In one aspect, there is provided an apparatus for determining a material characteristic of a material comprising: a fluid device comprising: a main channel adapted to receive a flowing material therethrough; a branch channel connected to the main channel, wherein the flowing material communicates pressure to from the main channel to the branch channel; a first stimulator configured to apply a first stimulus to modulate a material property parameter of material within a first space of the branch channel; a second stimulator configured to apply a second stimulus to modulate the material property parameter of material within a second space of the branch channel; a first sensor configured to sense a material characteristic of the material within the first space of the branch channel; and a second sensor configured to sense the material characteristic of the material within the second space of the branch channel.

In some embodiments, the first stimulator and the second stimulator, independently, comprise a temperature modulator. In some embodiments, the first stimulator and the second stimulator comprise the same temperature modulator, wherein a first portion of the temperature modulator is configured to apply the first stimulus and a second portion of the temperature modulator is configured to apply the second stimulus. In some embodiments, the temperature modulator comprises a Peltier device, a heat exchanger, a heating element, or combination thereof. In some embodiments, the temperature modulator comprises a heat exchanger.

In some embodiments, the device comprises a sensory layer and an etched layer joined to the sensory layer, wherein the volume of the main channel and the volume of the branch channel are defined by void space between the sensory layer and the etched layer. In some embodiments, a front side of the etched layer comprises at least a portion the main channel and at least a portion of the branch channel and a rear side of the etched layer comprises at least a portion of the heat exchanger such that the at least a portion of the main channel and the at least a portion of the branch channel are integral with the at least a portion of the heat exchanger.

In some embodiments, the device comprises a plurality of cells, each one of the first plurality cells connected independently to the branch channel.

In some embodiments, the device further comprises: a downstream branch channel, wherein the downstream branch channel connects to the main channel downstream of the branch channel, wherein the apparatus further comprises: a first downstream stimulator configured to apply a third stimulus to modulate a material property parameter of material within a first space of the downstream branch channel; a second downstream stimulator configured to apply a fourth stimulus to modulate a material property parameter of material within a second space of the downstream branch channel; a first downstream sensor configured to sense the material characteristic of the material within the first space of the downstream branch channel; and a second downstream sensor configured to sense the material characteristic of the material within the second space of the downstream branch channel.

In some embodiments, the device comprises a second plurality of cells, each one of the second plurality of cells connected independently to the downstream branch channel.

In some embodiments, the sensor is comprises an optical sensor, a spectrometer, a fluorometer, a Raman microscope, a refractometer, or any combination thereof.

In some embodiments, the device is a microfluidic device. In some embodiments, the device is a nanofluidic device.

BRIEF DESCRIPTION OF DRAWINGS

The present invention is further described in the detailed description which follows, in reference to the noted plurality of drawings by way of non-limiting examples of exemplary embodiments of the invention, in which:

FIG. 1 illustrates a method according to an embodiment of the invention;

FIG. 2 illustrates a method according to an embodiment of the invention;

FIG. 3 illustrates a method according to an embodiment of the invention;

DETAILED DESCRIPTION

Figure 4:
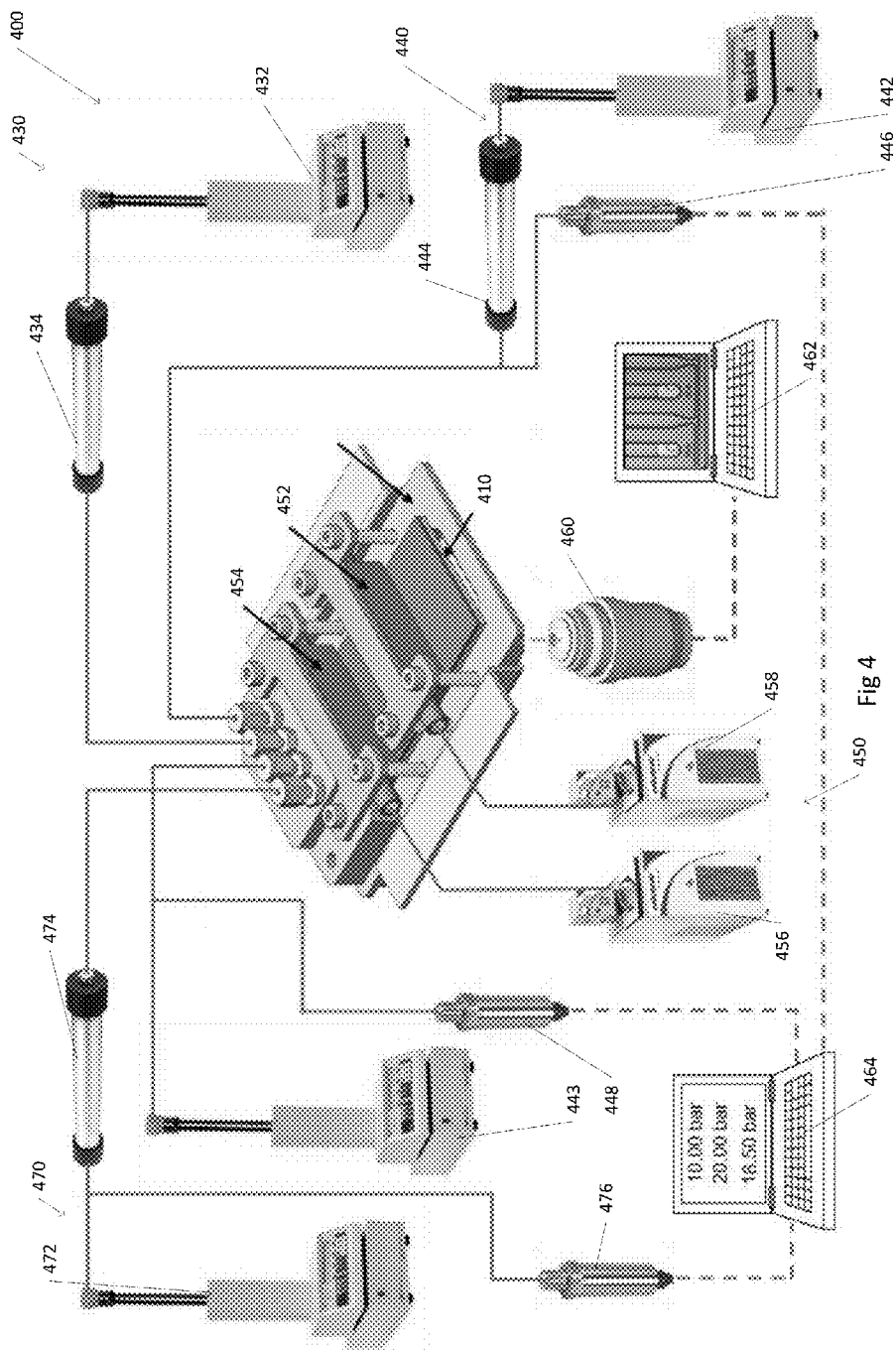
FIG. 4 is a schematic diagram of an apparatus according to an embodiment of the invention.

Having reference to FIG. 1, in one aspect of the invention, a method 100 is provided for determining a material characteristic of a sample material.

At block 102, the sample material is loaded into a plurality of cells. In some embodiments, the same sample material is loaded to each one of the cells. In some embodiments, each one of the cells is fluidly connected to a channel. The sample material is loaded into the plurality of cells through the channel.

In some embodiments, the sample material is supplied from a sample material reservoir. In some embodiments, the sample material is flowed from the sample material reservoir to the plurality of cells via an inlet of the channel. In some embodiments, the channel includes an outlet. In some embodiments, the outlet is configured to circulate the sample material and/or remove undesired material from the channel (e.g. acting as a bleed).

In some embodiments, the sample material is an oil reservoir material, a biological material, a biomedical material, an environmental material, or a combination thereof. In some embodiments, the sample material comprises a mixture of compounds. In some embodiments, the mixture of compounds comprises a mixture of hydrocarbon compounds.

At block 104, an interference material is disposed relative to the sample material such that the interference material at least retards the transport of the sample material from a one of the cells to at least another one of the cells.

In some embodiments, the interference material prevents or substantially prevents the transport of sample material from a one of the cells to at least another one of the cells. In some embodiments, the prevention or substantial prevention of transport of the sample material from a one of the cells to at least another one of the cells confines sample material within a cell to that cell.

The selection of interference material may be based on a number of factors. These factors generally relate to the ability of the interference material to retard the transport of the sample material. These factors include miscibility, wetting characteristics, reactivity, viscosity and surface tension, the ability to transmit pressure, economic considerations, and health.

The transport of the sample material from the one of the cells to the at least another one of the cells may be visualized as a series of steps. In some embodiments, the disposition of the interference material creates an interface between the sample material and the interference material. Thus, in some embodiments, the transport being retarded includes the transport across the interface between the sample material and the interference material.

The miscibility of the sample material with the interference material affects the ability of the sample material to mix with the interference material. If the sample material and the interference material are miscible, the sample material may dissolve into the interference material at the interface. The immiscibility or substantial immiscibility of the sample material and the interference material tends to reduce transport in this manner. In some embodiments, the sample material is immiscible or substantially immiscible relative to the interference material. In some embodiments, the interference material is sufficiently immiscible with all components of the sample material such that transport from the sample fluid to the interference material, during the period from the initiation of the disposing of the interference material begins until the end of the sensing, is negligible. In some embodiments, if one or more components of the sample diffuse into the interface material, or vice versa, the disposing of the interference material, the applying of the stimulus, the sensing of the material characteristic and/or the determining of the phase behaviour (described in more detail below) may be performed with consideration of the transport and associated concentration changes. For example, in some embodiments, the applying the stimulus and the sensing of the material characteristic are performed shortly after the interference material is disposed, thereby minimizing transport-related variation.

Surface interactions at the interface between the sample material and the interference material also affect this transport. For example, where the sample material is a gas and the interference material is a liquid, surface interactions can cause the sample material to "break through" the interface, resulting in the generation of bubbles of the sample material in the interference material. When the surface tension between the sample material and the interference material is increased, the bubble generation is reduced. In some embodiments, the interference material has a surface tension of 0.01-10 N/m. In some embodiments, the surface tension is 0.047 N/m. In some embodiments, the interference material comprises a surface tension altering additive. In some embodiments, the surface tension altering additive is a surfactant, salt, or combination thereof.

Bulk transport, such as by convection, and molecular transport, such as by diffusion, may transport any sample material that crosses the interface between the sample material and the interference material through the interference material. One factor affecting this transport is the viscosity of the interference material. In some embodiments, the viscosity of the interference material is from 0.1 cP to 100 cP. In some embodiments, the viscosity of the interference material is 14 cP.

The relative wetting characteristics of the interference material and the sample material with respect to the cell affects the ability of the sample material to "leak" around the interference material. Where the interference material has higher contact angle with the cell than the sample material, adhesive forces between the sample material and the cell may allow the sample material to be transported around the interference material. For example, in some systems having cells made from silicon and glass, gallinstan (a liquid metal alloy of gallium, indium, and tin) has poor wettability characteristics and there are challenges in using it as an interference material. The poor wettability characteristics can lead to the sample material leaking around the gallinstan, for example, around corners or junctions of channels, causing the gallinstan to form fluid segments such that there is more than a single interface with the sample material. Thus, in some embodiments, the contact angle between the interference material and the cell is lower than a contact angle between the sample material and the cell. In some embodiments, the cell is treated to improve the wettability characteristics of the interference material. In some embodiments, the cell comprises a coating for improving the wettability characteristics of the interference material.

Small changes in composition may have pronounced effects on the properties of the sample fluid. Reactions that occur between the sample fluid and the interference material may change the composition of the sample material. For example, where the sample material is a mixture of compounds, where one compound preferentially reacts with the interference material, the reaction would alter the mass ratios of the mixture compounds. Further, the reaction may produce additional compounds that can alter the composition of the sample material. Further still, where different cells are subject to different stimulus, for example, where different temperatures are applied to each cell, the reaction kinetics between the sample fluid and the interference material may be altered for each cell, such that the sample material in each cell would have a different composition, creating additional challenges when determining properties of the sample fluid. Thus, in some embodiments, the interference material is chemically inert with respect to the sample material.

In some embodiments, the interference material is a fluid or a pumpable gel. In some embodiments, the interference material is a liquid, gas, or plasma. In some embodiments, the interference material is a liquid. In some embodiments, the liquid is an incompressible liquid. In some embodiments, the interference material is liquid metal, ethylene glycol, glycerol, oil, or a mixture thereof. In some preferred embodiments, the interference material is ethylene glycol.

At block 106, for each one of the cells, independently, a stimulus is applied to the sample material in the cell such that a conditioned sample material is obtained. In some embodiments, by applying an independent stimulus to the sample material in each cell, the conditioned sample material in each cell is at different condition.

In some embodiments, the applied stimulus modulates a material property of the sample material. By applying a respective stimulus to the sample material for each one of the cells, the modulated material property of the conditioned sample material of each one of the cells may be different. In some embodiments, the modulated material property is an intensive property. In some embodiments, the modulated material property comprises pressure, temperature, radiation dose, voltage, electric field, magnetic field, or any combination thereof. Thus, in some embodiments, the conditioned sample material in each one of the cells is independently disposed at a modulated pressure, temperature, radiation dose, voltage, electric field, magnetic field, or any combination thereof.

In those embodiments where the stimulus modulates pressure, the stimulus may be applied by the interference material. In some embodiments, the interference material is a fluid that is pressurized, and the pressure is communicated by the interference material to the sample material in each one of the cells.

In some of those embodiments where the sample material is loaded into the cells via the channel, the interference material is supplied into the channel after the sample material is loaded into the cells. In some embodiments, pressurizing the interference material loaded into the channel will communicate the pressure to the sample material in each of the cells.

In some embodiments, the interference material is continuously flowed into the channel via an inlet, and is continuously flowed out of the channel via an outlet. In some embodiments, the channel includes a main channel. In some embodiments, the main channel includes the inlet and the outlet. In these embodiments, the pressure at the inlet will be disposed at an inlet pressure and the pressure at the outlet will be disposed at an outlet pressure. Frictional losses due to the fluid flow in the channel tend to create a pressure drop in the channel along the direction of flow. In some embodiments, the pressure in the main channel is higher at an upstream location than at a downstream location. As such, in some embodiments, an upstream cell connected to the main channel has a higher pressure than a downstream cell connected to the main channel. In some embodiments, the main channel includes a fluid resistor placed between an upstream location and downstream location for decreasing the pressure of a fluid flowing therein.

In some embodiments, the channel includes a branch channel that connects to the main channel. In some embodiments, the disposition of the interference material results in the placement of at least a portion of the interference material in the branch channel. In some embodiments, the branch channel is configured such that when the interference material is flowed from the inlet of the main channel to the outlet of the main channel, the interference material communicates pressure to the branch channel. In some embodiments, the pressure is communicated such that the pressure is substantially constant in the branch channel. In such embodiments, the sample material contained within each cell connected to the branch channel is disposed at the same pressure. In some embodiments, the branch channel is closed such that the branch channel defines an enclosed volume or a dead volume. In some embodiments, the branch channel has an outlet configured such that for a fluid flowing through the channel, the flow rate at the outlet of the main channel is greater than the flow rate at the outlet of the branch channel.

In some embodiments, the channel includes a downstream branch channel connected to the main channel downstream of the branch channel. In some embodiments, the downstream branch channel may be configured similarly to the branch channel. In some embodiments, the disposing of the interference material results in the placement of at least a portion of the interference material in the downstream branch channel. In some embodiments, the downstream branch channel is configured such that when the interference material is flowed from the inlet of the main channel to the outlet of the main channel, the interference material communicates pressure to the downstream branch channel. In some embodiments, the pressure is communicated such that the pressure is substantially constant in the downstream branch channel. In such embodiments, the sample material contained within each cell connected to the downstream branch channel is disposed at the same pressure. In some embodiments, the downstream branch channel is closed such that the downstream branch channel defines an enclosed volume. In some embodiments, the downstream branch channel has an outlet configured such that for a fluid flowing through the channel, the flow rate at the outlet of the main channel is greater than the flow rate at the outlet of the downstream branch channel.

In some embodiments, the pressure at the connection point between the branch channel and the main channel is higher than the pressure at the connection point between the downstream branch channel and the main channel due to frictional losses associated with the flow of the interference material in the channel. In some embodiments, the fluid resistor is disposed between the branch channel and the downstream branch channel. In some embodiments, the main channel includes the fluid resistor.

In some embodiments, a pump upstream of the inlet of the main channel, a pump downstream of the outlet of the main channel, or both modulate the flow of the interference material in the main channel. In a preferred embodiment, the flow of the interference material in the main channel is modulated by both an upstream pump and a downstream pump. Such dual-pump configurations allow better control of the pressure of the interference material in the channel. In such embodiments, the viscosity of the interference material must not be so high that it is prevents or substantially prevents the interference material from being pumped.

In some embodiments, the pressure is modulated to each one of the cells such that the range of pressures being applied is in a zone of interest. In some embodiments, the range of pressures being applied is between 0 MPa and 20 MPa. In some embodiments, the range of pressures being applied is between 0 MPa and 8 MPa.

The zone of interest may depend on the sample material being examined. For example, where the sample material is an oil reservoir material, the zone of interest may be varied to simulate potential operating pressures and temperatures for extracting the oil reservoir material from an underground reservoir. In some embodiments, for example, where the sample material is 20% methane and 80% propane, the pressure of the conditioned sample material is between 0.6 MPa to 7.0 MPa. In some of these embodiments, the pressure is of the conditioned sample material is between 0.6 MPa and 6.5 MPa. In some embodiments, for example, where the sample material is propane, the pressure of the conditioned sample material is between 5.0 MPa and 7.5 MPa. In some embodiments, for example, where the sample material is $CO_2$, the pressure of the conditioned sample material is between 5.5 MPa and 8.0 MPa.

Further, in some embodiments, the zone of interest may be subsequently "zoomed in" such that the sample material in the cells is modulated to a subrange of initially applied pressures. By "zooming in" on a subrange, the measurement of material characteristics may be more precise as there may be smaller variation in the pressure between different cells of the plurality. In some embodiments where the sample material is 20% methane and 80% propane, the pressure of the conditioned sample material is between 0.6 MPa to 7.0 MPa and is subsequently "zoomed in" by modulating the stimulus applied to the sample material in the cells such that the pressure of the conditioned sample material is between 5.0 MPa and 7.0 MPa.

In some embodiments, the modulated material property is temperature. In some embodiments, the temperature is modulated using a Peltier, a heat exchanger, a heating element, a laser, an optical heater, or combination thereof.

In a preferred embodiment, the temperature is modulated using a heat exchanger. The heat exchanger can be used to heat or cool the sample material within a cell depending on the heat exchange medium being used. In some embodiments, the temperature of the heat exchange medium entering the heat exchanger is controlled. In some embodiments, one heat exchanger may be used to modulate the temperature of multiple cells of the plurality. In some of these embodiments, the heat exchange medium is flowed through the heat exchanger such that a temperature gradient is created in the heat exchanger. In some of these embodiments, the temperature gradient modulates the temperature such that the sample material within each cell of the plurality to which the heat exchanger applies the stimulus is modulated to a respective temperature. For example, when a heat exchanger is used to heat up sample material, the heat exchange medium may be cooled as it flows through the heat exchanger. This can cause the sample material in some cells to be modulated to a lower temperature as compared the sample material in other cells. In other embodiments, the flow of the heat exchange medium is flowed through the heat exchanger such that there is minimal variation in the temperature of the heat exchange medium. In some of these embodiments, the sample material in cells where the temperature is modulated by the heat exchanger will be modulated to approximately the same temperature.

In some embodiments, multiple heat exchangers are used to modulate the temperature of sample material in the plurality of cells. In some embodiments, a first heat exchanger modulates the temperature of sample material within some of the cells to a first temperature, and a second heat exchanger modulates the temperature of sample material within some other of the cells to a second temperature.

In some embodiments, at least a portion of each one of the cells is connected to a common thermally conductive plate. In some embodiments, the thermally conductive plate is a silicon chip etched such that at least a portion of each one of the cells comprises a portion of the silicon chip. For example, in a silicon chip where a portion has been removed, such as by etching, the walls of the chip created by the removal of silicon form part of a wall of the cell.

In some of the embodiments where a common thermally conductive plate is present, the modulating of the temperature of the cells is effected by two temperature modulators. In such embodiments, a first temperature modulator modulates the temperature of one portion of the plate to a first temperature, and a second temperature modulator modulates the temperature of another portion of the plate to a second temperature. Since the first portion of the plate is modulated to a first temperature, the sample material of cells disposed proximate the first portion will be modulated to approximately the first temperature. Similarly, since the second portion of the plate is modulated to a second temperature, the sample material of cells disposed proximate the second portion will be modulated to approximately the second temperature. Where the first temperature and the second temperature are different temperatures, a thermal gradient is established in the thermally conductive plate. The temperature of sample material in any particular cell of the plurality will vary according its position relative to the first and the second portion. In some embodiments, the geometry of the cells is configured to reduce the gradient of the temperature within each cell. For example, a cell may be disposed on the common thermally conductive plate such that a thermal gradient exists across its width. Accordingly, in some embodiments, the width of the cell may be minimized to reduce the gradient within the cell. Further, the shape of the cell may be selected to reduce thermal gradients across the cell. For example, for the same volume of sample material contained within a cell, there may be a larger gradient in a cell having a circular profile than a cell having an elongate profile. In some embodiments, the cell is has an elongate cylindrical or prismatic profile. In some embodiments, the width of each cell is between 5 nm and 200 µm. In some embodiments, the width of each cell is between 10 nm and 100 µm. In some embodiments, the cells comprise a width of between 5 µm and 100 µm. In some embodiments, for example, in a microfluidic device, the width of the cell is 100 µm. In some embodiments, for example, in a nanofluidic device, the width of the cell is 5 µm.

In some embodiments at least a portion of the heat exchanger is integral with at least a portion of the cell. In some embodiments, the sample material is disposed on one side of a cell wall and a heat exchange material is flowed on the other side of the cell wall. In some embodiments where there is a common thermally conductive plate, the cells are disposed on one side of the thermally conductive plate a heat exchange material is flowed across the other side of the plate.

In some embodiments, the thermally conductive plate comprises high thermal conductivity. In some embodiments, the thermally conductive place has low reactivity with the sample material, the heat exchange medium, or both. In some embodiments, the thermally conductive plate comprises metal. In some embodiments, the metal comprises stainless steel, copper, aluminum, silicon, or a combination thereof. In some embodiments, the thermally conductive plate is silicon.

In some embodiments, the temperature is modulated to each one of the cells such that the range of temperatures being applied is in a zone of interest. In some embodiments, the range of temperatures is between −10° C. and 500° C. In some embodiments, the range of temperatures is between −10° C. and 200° C.

As noted previously, the zone of interest may depend on the sample material being examined. For example, in some embodiments, where the sample material consists of 20% methane and 80% propane, and the temperature of the conditioned sample material is between 22° C. and 88° C. In some embodiments, for example, where the sample material is propane, the temperature of the conditioned sample material is between 18° C. and 32° C.

Further, in some embodiments, the zone of interest may be subsequently "zoomed in" such that the sample material in the cells is modulated to a subrange of initially applied temperatures. By "zooming in" on a subrange, the measurement of material characteristics may be more precise as there may be smaller variation in the temperature between different cells of the plurality. For example, in some embodiments, where the sample material consists of 20% methane and 80% propane, and the temperature of the conditioned sample material is between 22° C. and 88° C., the temperature is subsequently "zoomed in" by modulating the stimulus applied to the sample material in the cells such that the temperature of the conditioned sample material is between 68° C. and 87° C.

In some embodiments, the channel includes a series of branch channels. In some embodiments, the previously described branch channel is the first of the series of branch channels and the downstream branch channel is the second of the series of branch channels. Each branch channel of the series of branch channels connects to the main channel downstream of the previous branch channel of the series. In some embodiments, the series of branch channels are parallel. In some embodiments, the series of branch channels extend from the main channel in the same direction. In some embodiments, the series of branch channels are parallel and co-extensive. In some embodiments, for example, the parallel and co-extensive series of branch channels are configured such that cells connected to the channel are disposed in a two dimensional array.

In such embodiments, one modulated material property is varied along one dimension of the array and another modulated material property is varied along another dimension. For example, pressure is varied across one dimension of the array and temperature is varied across another dimension. In some embodiments, pressure is varied across one dimension such that each branch channel of the series of branch channels is disposed at a different pressure than another branch channel of the series of branch channels, and the pressure within each branch channel is substantially constant. In some embodiments, since the flow of the interference material in the main channel causes a pressure drop in the main channel, each branch of the series of branch channels is disposed at a lower pressure than a branch of the series that connects to the main channel upstream thereof. In some embodiments, the series of branch channels is configured such that there is a linear, logarithmic, or exponential decrease in the pressure from one branch of the series to the next of the series. In some embodiments, the temperature is varied across one dimension. In some embodiments, the temperature is varied within a branch channel based on the distance from connection between the branch channel and the main channel. For example, a conditioned sample material within a cell of a branch channel, where the cell is disposed 500 μm away from the connection between the main channel and the branch channel will be the same temperature of a conditioned sample material within a cell of another branch channel, if that cell is also disposed 500 μm away from the connection between the main channel and its respective branch channel. In some embodiments, the temperature is varied such that the temperature is higher in the branch channel at distances further away from the main channel. In some embodiments, the temperature is varied such that the temperature is lower in the branch channel at distances further away from the main channel.

In some embodiments, the cells are designed to reduce a conditioning time to condition a sample material disposed within a cell to obtain a conditioned sample material. For example, where the stimulus is heat for modulating the temperature of a sample material, the wall of the cell may be heated. In a small cell, less time is generally required to condition the sample material because there are typically smaller distances for molecules to travel in the cell's interior and less mass contained within the cell. In contrast, in a large cell, the sample material generally requires more time to be conditioned because there is more mass contained within the cell and there are larger distances for molecules to travel. In some embodiments, the conditioned sample is obtained after a few seconds of the applying of the stimulus. In some embodiments, the cells are microfluidic or nanofluidic cells. In some embodiments, the volume of each of the cells is between $1\times10^{-8}$ and 1 mm$^3$. In some embodiments where the cells are microfluidic cells, the volume of each cell is between $1\times10^{-4}$ mm$^3$ and 1 mm$^3$. In some embodiments where the cells are microfluidic cells, the volume of each cell is $3\times10^{-3}$ mm$^3$. In some embodiments where the cells are nanofluidic cells, the volume of each cell is between $1\times10^{-8}$ mm$^3$ and $1\times10^{-4}$ mm$^3$. In some embodiments where the cells are nanofluidic cells, the volume of each cell is $1\times10^{-8}$ mm$^3$. In embodiments where at least a portion the cells are integral with an etched layer, the height of a cell is related to the depth of the etched portions. In some embodiments the height of each cell is at most 1 mm. In some embodiments, the height of each cell is between 5 nm and 200 μm. In some embodiments, the height of each cell is between 10 nm and 100 μm. In some embodiments, for example, in a microfluidic device, the height of each cell is 15 μm. In some embodiments, for example, in a nanofluidic device, the height of each cell is less than 100 nm. In some embodiments, the length of each cell is 2000 μm. In some embodiments, each cell has a length to height ratio of between 1000000:1 and 5:1. In some embodiments, each cell has a length to height ratio of about 67:1. In some embodiments, each cell has a length to width ratio of between 1000000:1 and 5:1. In some embodiments, each cell has a length to width ratio of about 10:1.

In addition to equilibration time, micro- and nano-fluidic cells have other benefits. For example, a force exerted on an object is a function of pressure and area. In PVT cells of the prior art, due the high pressures at which the cells often operate, significant consideration must be given to ensuring the safe operation of the cell since equipment accidents and failure may have catastrophic consequences. By miniaturizing the cells according to some embodiments of the present invention, the forces are reduced due to smaller surface areas being present. This may reduce the complexity of operation and of the equipment being used. Further, as the sizes of the channels present are relatively small, the flow through the channels is more likely to be disposed in a laminar flow regime. When fluids are flowing according to a laminar flow regime, the flow is more stable and the fluid pressure is better predicted and controlled as compared to a turbulent flow regime. In some embodiments, the interference material is flowed through the main channel such that it has a Reynolds number of less than 2000. In some embodiments, the interference material is flowed through the main channel such that it has a Reynolds number of less than 1000. Further still, the sample material may exhibit different phase properties at the nano-scale than it does at macroscopic and even microscopic scale. For example, hydrocarbon material in an underground reservoir may be disposed in pores of the formation having nano-scale diameters. The phase property behaviour of such material may not be properly predicted in such environments when traditional PVT or even micro-fluidic devices are used to characterize the material.

The geometry of the cell may also affect the conditioning time. If a stimulus is transferred to a sample material in a cell through the cell wall, a relatively larger amount of the sample material being in contact with the cell wall will decrease the conditioning time. In some embodiments, the ratio of the internal surface area of the cell to the volume of the cell is between $1\times10^{-6}$ nm$^{-1}$ and 1 nm$^{-1}$. In some embodiments, the ratio of the internal surface area of the cell to the volume of the cells is about 0.154 nm$^{-1}$.

The interference material, by at least retarding the transport of sample material from one cell to another cell, helps to determine phase behaviour for sample materials that are mixtures. For example, where the sample material is conditioned to a temperature and pressure that is between the dew point and the bubble point, the composition of the gas and liquid phase of the sample material varies depending on the temperature and pressure. If gas from another cell were to be transported into the cell, the gas from the other cell, which may have been equilibrated at different conditions in the phase envelope, can change the overall composition of sample material in the cell and affect the phase behaviour. When a sample material is disposed in a branch channel at a constant pressure with a range of temperatures present across the branch channel and no interference material is placed in the branch channel, if two fluid phases exist at that pressure and at any of the temperature conditions within the range, mass may be transported within the channel such that one phase accumulates on one side of the branch channel and the other phase accumulates in the other side of the branch channel. In this manner an interface between the two phases is established. The temperature at the interface may, for example, correspond to the boiling point for a single-component sample material. However, for a sample material having a mixture of compounds, the dew point and boiling point for the sample material cannot be determined based on the conditions at interface. In some embodiments, by disposing the interference material to retard transport across cells, the sensing of each cell, having stimulus applied to obtain conditioned material disposed at a different condition, can be used to determine the conditions at which condensation or a bubble first forms, or at which the interfacial tension decreases to zero (at the critical point).

At block 108, for each one of the cells, independently, a material characteristic of the conditioned sample material is sensed.

In some embodiments, the material characteristic is a state of matter, or a volume ratio between phases of the sample material within a cell, or a combination thereof. This information can be processed to determine additional phase behaviour parameters of the sample material. In some embodiments, the material characteristic of the sample material is used to determine a critical point, melting point, boiling point, eutectic point, cricondentherm, cricondenbar, dew point, bubble point, quality lines, or combinations thereof. In some embodiments, a phase diagram is generated using the sensed material characteristics.

For example, where temperature and pressure are varied, a state of matter can be sensed for various temperature and pressure conditions. For a conditioned sample material having a pressure just below the dew point line, the conditioned sample material would be a gas. For a conditioned sample material having a temperature and pressure within a phase envelope defined by the bubble point line and the dew point line, the conditioned sample material would be present in the cell as both a liquid and a gas. For a conditioned sample material having a pressure above the bubble point line, the conditioned sample material exists as a liquid.

Figure 13:
FIG. 13 is a photograph illustrating the phase determination in a nano-fluidic device according to an embodiment of the invention.

In some embodiments, for conditioned sample material having modulated properties near the bubble point line or the dew point line, the interface between the conditioned sample material and the interference material appear to be optically "thicker" than a conditioned sample having properties further from the bubble point line or the dew point line. Without necessarily being bound by theory, it is believed that the "thick" interface is caused by optical interference by bubble formation or condensation. For example, for a liquid mixture where the pressure has been lowered to the bubble point, gas bubbles may begin to form. It is thermodynamically favourable to form at nucleation sites. In some embodiments, an interface between the liquid mixture and a liquid piston exerting pressure thereon may provide such sites. Thus, the initial formation of bubbles may occur at such interfaces. For example, with reference to FIG. 13, a series of wells at the same pressure are imaged, cropped and re-oriented and displayed as a continuous mosaic where temperature increases left to right. Each well includes ethylene glycol as an interference material, and a sample material having a liquid and/or a vapour phase. The vapor bubbles are smaller on the left, where there is also a liquid phase. At higher temperatures (right), there is no liquid phase. In some embodiments, the pixel intensity is measured and compared along a vapor-liquid film-ethylene glycol (line 1300) for each well to determine where the liquid film disappears, which corresponds to the dew point line.

In some embodiments, the sensing is performed through a sensory portion of the cell. In some embodiments, the sensory portion permits the transmission of electromagnetic radiation therethrough. In some embodiments, the sensory portion is optically transparent. In some embodiments, the sensory layer is glass, plastic, transparent ceramic. In some embodiments, the sensory layer is a material compatible with the pressures and temperatures of the methods of the present invention.

In some embodiments, the method utilizes a device having a sensory layer and an etched layer bonded such that the volumes of the cells are defined by the sensory layer and the etched layer. In some embodiments, a void space between the sensory layer and the etched layer forms the volume of a cell. In some embodiments, the sensory layer comprises the sensory portion of each one of the cells. In some embodiments, the etched layer comprises the common thermally conductive plate.

In some embodiments, the sensing comprises optical sensing, fluorescence sensing, Raman spectroscopy, conductivity sensing, or any combination thereof. In some preferred embodiments, the sensing comprises optical sensing. In some embodiments, the optical sensing senses light transmitted through the conditioned sample. In some embodiments, sample is "front lit" where a light source is located on the same side of the cell as the sensor. In some embodiments, the sample material is "back lit" where a light source is located on the opposite side of the cell as the sensor. In some embodiments, the sensing of the light transmitted through the conditioned sample material is used to determine the state or states of matter of the conditioned sample material.

In some embodiments where the conditioned sample material is present in the cells in more than one phase, one phase transmits more light than another phase. In some embodiments, for example, where the conditioned sample material is present as a gas and a liquid, less light is transmitted through the liquid than the gas. In other embodiments, for example, less light is transmitted through the gas than the liquid. In some embodiments, the colour of the gas is different from the colour of the liquid. Although, due to density differences, liquids tend to transmit less light therethrough than a gas, the properties of the cells can cause light interference, diffraction, refraction, or some combination thereof, such that the sensor senses less light being transmitted through the gas than through the liquid. In some embodiments, the conditioned sample material is present as a gas, liquid, solid, or any combination thereof.

Figure 12:
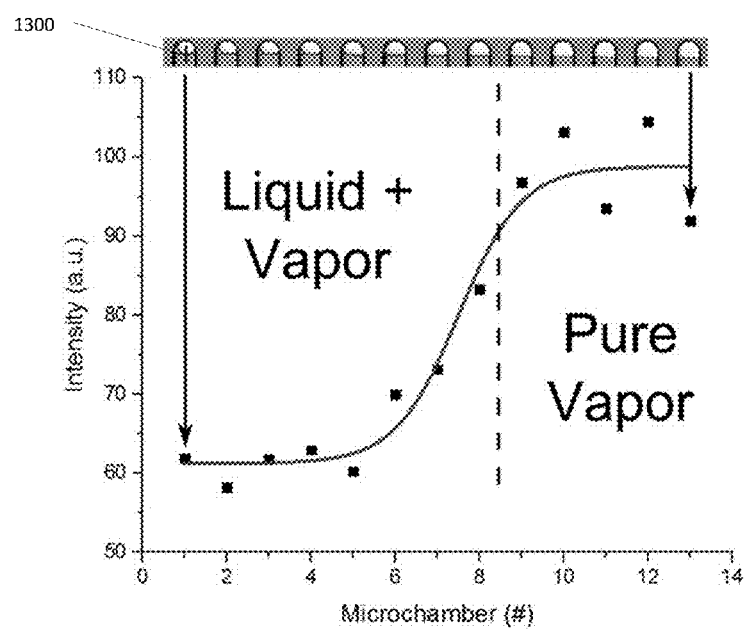
FIG. 12 is a chart illustrating the determination of a dew point line of a sample material according to an embodiment of the invention.

In some of those embodiments where the device is a nanofluidic device, the device comprises a refractive layer. As dimensions of each cell in a nanofluidic device may be very small, a refractive layer helps the sensor sense the material characteristic of the conditioned sample material. For example, where an optical sensing is performed, the refractive layer can refract light such that a vapour is resolved as a red area and a liquid is resolved as a purple area (a black and white conversion of such an image is shown in FIG. 12 where the red area is shown as being lighter than the purple area).

In some embodiments, the sensing generates sensory data. In some embodiments, the sensory data is processed to generate phase behaviour data for the sample material.

In some embodiments, the material characteristic of the sample material in the cells are sensed sequentially, simultaneously, and/or concurrently. In some embodiments, the sensing is performed by a single sensor. In some embodiments, the single sensor senses the material characteristic of all of the cells simultaneously. In some embodiments, the single sensor senses the material characteristic of some of the cells simultaneously. In some embodiments, the single sensor senses the material characteristic of each cell individually. In some embodiments, the sensing is performed by a plurality of sensors. In some embodiments, the material characteristic of each one of the cells is sensed by a corresponding sensor.

In another aspect, a method 200 is provided for determining a material characteristic of a material.

At block 202, a material is flowed through a main channel such that a first pressure is established and is communicated to a branch channel from the main channel.

In some embodiments, the main channel includes the inlet and the outlet. In these embodiments, the pressure at the inlet will be disposed at an upstream pressure and the pressure at the outlet will be disposed at a downstream pressure. Frictional losses due to the fluid flow in the channel tend to create a pressure drop in the channel along the direction of flow. In some embodiments, the pressure in the main channel is higher at an upstream location than at a downstream location.

In some embodiments, the pressure is communicated such that the pressure is substantially constant in the branch channel. In some embodiments, the branch channel is closed such that the branch channel defines an enclosed volume. In some embodiments, the branch channel has an outlet configured such that for a fluid flowing through the channel, the flow rate at the outlet of the main channel is greater than the flow rate at the outlet of the branch channel.

At block 204, a first stimulus is applied to material within a first space of the branch channel for modulating a material property of the material within the first space of the branch channel.

In some embodiments, the modulated material property of the material within the first space of the branch channel is temperature, received radiation, voltage, electric field, magnetic field or a combination thereof.

In some embodiments, the modulated material property is temperature. In some embodiments, the temperature is modulated using a Peltier, a heat exchanger, a heating element, a laser, an optical heater, or combination thereof.

In some embodiments, the temperature is modulated using a heat exchanger. The heat exchanger can be used to heat or cool the sample material within a space of the branch channel depending on the heat exchange medium being used. In some embodiments, the temperature of the incoming heat exchange medium is controlled. In some embodiments, the temperature of the outgoing heat exchange medium is controlled by increasing the flow rate of the heat exchange medium.

In some embodiments at least a portion of the heat exchanger is integral with the branch channel at the first space. In some embodiments, the sample material is disposed on one side of the branch channel and a heat exchange material is flowed on the other side of the branch channel. In some embodiments where there is a common thermally conductive plate, the branch channel is disposed on one side of the thermally conductive plate a heat exchange material is flowed across the other side of the plate.

In some embodiments, the thermally conductive plate comprises high thermal conductivity. In some embodiments, the thermally conductive place has low reactivity with the sample material, the heat exchange medium, or both. In some embodiments, the thermally conductive plate comprises metal. In some embodiments, the thermally conductive plate comprises silicon.

At block 206, a second stimulus is applied to material within a second space of the branch channel for modulating a material property parameter of the material within the second space of the branch channel. In some embodiments, the second stimulus is applied concurrently with the first stimulus. In some embodiments, the second stimulus is applied simultaneously with the first stimulus.

In some embodiments, the modulated material property of the material within the second space of the branch channel is temperature, received radiation, voltage, electric field, magnetic field, or a combination thereof. In some embodiments, the modulated material property of the material within the first space of the branch channel is the same modulated material property of the material within the second space of the branch channel, but is modulated to a different condition. In some embodiments, the first stimulus and the second stimulus modulate the temperature of the materials at the first space and the second space, respectively, but are conditioned to different temperatures.

In some embodiments where the first stimulus and the second stimulus modulate the same material property, the first stimulus and the second stimulus are applied by the same modulator. In some embodiments where the same modulator is a heat exchanger, the flow of the heat exchange material is parallel to the branch channel. In such embodiments, as heat is transferred, the heat exchange material will heat up or cool down, depending on the heat transferred between the heat exchange material and the material within the branch channel. This tends to create a thermal gradient between different ends of the branch channel.

In some embodiments where at least a portion of the heat exchanger is integral with the branch channel at the first space, at least a different portion of the heat exchanger is integral with the second space.

In some embodiments, the first stimulus and the second stimulus modulate different material properties of the material within the first space and the second space. For example, in some embodiments, the first stimulus modulates the temperature of the material within the first space of the branch channel and the second stimulus modulates a radiation dose received by the material within the second space of the branch channel.

In some embodiments, the flowing of the material through the main channel establishes a second pressure downstream from the first pressure, and the second pressure is communicated to a downstream branch channel, the downstream branch channel connecting to the main channel downstream of the branch channel. In such embodiments, having reference to block 207A, a third stimulus is applied to material within a first space of the downstream branch channel for modulating a material property of the material within the first space of the branch channel, and, at block 207B, a fourth stimulus is applied to material within a second space of the downstream branch channel for modulating a material property of the material within the second space of the downstream branch channel. In such embodiments, the third and fourth stimuli are applied in a similar manner as the first and second stimuli.

In some embodiments, the branch channel and the downstream branch channel are substantially parallel, wherein the distance from the connection point of the main channel and the branch channel to the first space of the branch channel is about equal to the distance from the connection point of the main channel and the downstream branch channel to the first space of the downstream branch channel, and wherein the modulated material property of the material within the first space of the branch channel is modulated to a substantially equal condition to the modulated material property of the material within the first space of the downstream branch channel. In some embodiments, for a modulated material property, the material in any branch will be modulated to the same material property condition at the same axial displacement. For example, material within a space in a branch channel that is 500 μm from the connection between the branch channel and the main channel is modulated to 50° C. and material within a space in another channel that is 500 μm from the connection between that channel and the main channel is also modulated to 50° C.

Various combinations of modulators may be used to apply the first, second, third and fourth stimuli. In some embodiments, one modulator applies the first and third stimuli and another modulator applies the second and fourth stimuli. In some embodiments, one modulator applies the first, second, third and fourth stimuli.

In some embodiments, the flowed material is an interference material. In such embodiments, the branch channel comprises a first cell and a second cell, defining the first and second space of the branch channel, respectively. The material in the first space of the branch channel is a first sample fluid, and the material within the second space of the branch channel is a second sample fluid. In some embodiments, the first sample fluid and the second sample fluid have the sample composition. In some embodiments, the flowed fluid is an interference material that at least retards the transport of the first sample fluid from the first space of the branch channel to the second space of the branch channel, and at least retards the transport of the second sample fluid from the second space of the branch channel to the first space of the branch channel. Criteria for the selection of a suitable interference material is as described above.

At block 208, material characteristic of the material within the first space of the branch channel is sensed. At block 210, a material characteristic of the material within the second space of the branch channel is sensed.

Optionally, in those embodiments with a downstream branch channel, at block 211A, the material characteristic of the material within the first space of the downstream branch channel is sensed, and at 211B, the material characteristic of the material within the second space of the downstream branch channel is sensed.

In some embodiments, the sensing at blocks 208 and 210, and optionally 211A and 211B, may be performed in any order, and may be performed sequentially, simultaneously and/or concurrently.

Having reference to FIG. 3, in one aspect, there is provided a method 300 for determining a material characteristic of a material.

At block 302, a material is flowed through a main channel such that a first pressure is established and is communicated to a branch channel from the main channel, wherein the branch channel comprises a first space and a second space.

At block 304, a first stimulus is applied only to material within the first space of the branch channel for modulating a material property parameter of the material within the first space of the branch channel. This first stimulus is not applied to material within the second space of the branch channel. In some embodiments, mass and/or energy transport in the branch may affect the sample material disposed within the second space. In some embodiments, as the first stimulus is not applied to the second space, a gradient of the modulated property is formed across the branch channel. In some embodiments, there is little or no mass and/or energy transfer across material within the branch channel, such that the modulated property of material at the first space is at a condition which is discrete and different as compared to material in other spaces in the branch channel, such as the second space.

At block 306, a material characteristic of the material within the first space of the branch channel is sensed. At block 308, a material characteristic of material within the second space of the branch channel is sensed. As noted previously, in some embodiments, the order in which the sensing occurs may be varied. In some embodiments, the sensing at blocks 306 and 308 may be performed sequentially, simultaneously and/or concurrently.

Figure 5:
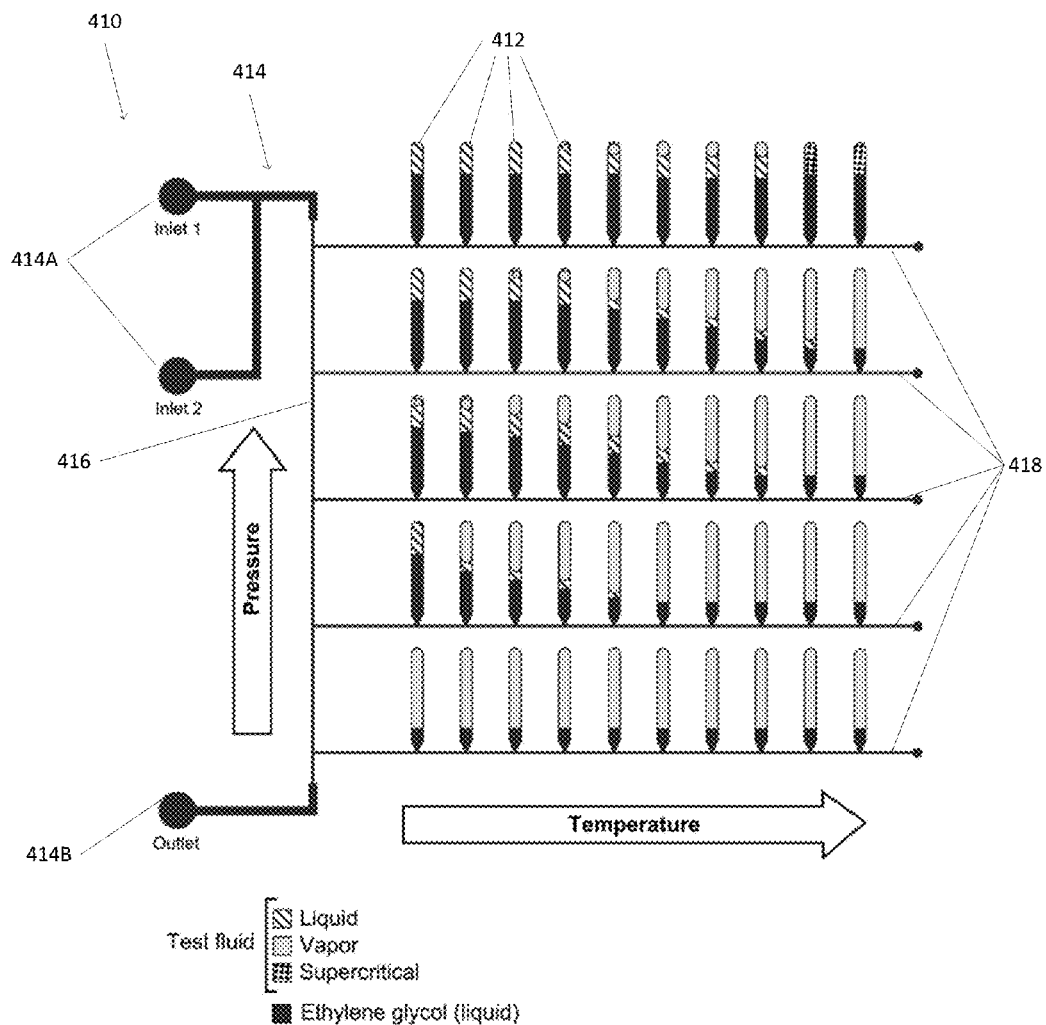
FIG. 5 is a schematic diagram of a fluid device according to an embodiment of the invention.

Having reference to FIG. 4, some embodiments of an apparatus 400 for determining phase properties of a sample material are provided. Apparatus 400 includes a device 410. The device 410 comprises a plurality of cells 412, and a channel 414 connected to the plurality of cells 412 (see FIG. 5). The channel 414 includes one or more inlets 414A and one or more outlets 414B. The channel 414 is configured to receive a flow of an interference material such that the interference material at least retards the transport of a sample material from one of the cells to another of the cells. The channel 414 includes a main channel 416 and branch channels 418 connected to the main channel.

Figure 6:
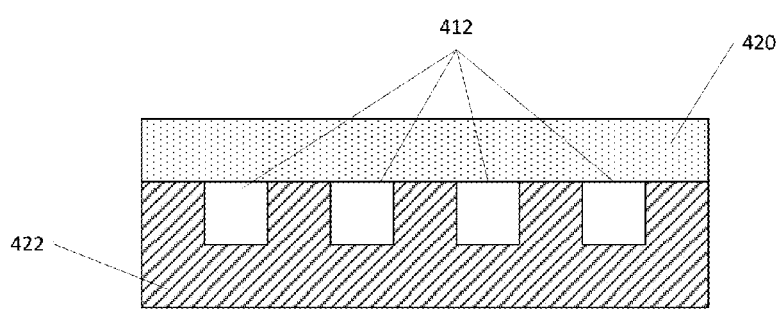
FIG. 6 is a cross sectional view of a portion of a fluid device according to an embodiment of the invention.

The device 410 includes a sensory layer 420 and an etched layer 422 joined to the sensory layer (see FIG. 6). At least a portion of the walls in the etched layer 422 formed by the etching, and the sensory layer 420 define the volumes of the cells 412.

A sample material module 430 includes a pump 432 configured to act on a sample material reservoir 434 to introduce sample material into device 410 through the inlet 414, thereby loading the sample material into the cells 412.

A pressure modulator 440 is configured to modulate the pressure within each cell applying an individual stimulus to each one of the cells to condition sample material disposed therein. The pressure modulator 440 includes a pump 442 configured to act on a cylinder 444, the cylinder 444 containing an interference material, to cause the interference material to flow into the device 410 via inlet 414A. A second pump 443 controls the flow of the interference material out of the outlet 414B of the device 410. Pressure transducers 446 and 448 are configured to monitor the pressure of the interference material near the inlet and outlet of the device. By varying the operation of pumps 442 and 443, pressure in the device 410 may be modulated.

A temperature modulator 450 is configured to modulate the temperature within the cells 412 by applying an individual stimulus to each one of the cells to condition the sample material disposed therein. The temperature modulator 450 includes a first portion 452 and a second portion 454 such that portions of the device in contact with the first portion 452 and the second portion 454 will be modulated to approximately a first and a second temperature. A heat exchange fluid is flowed through the first portion 452 and the second portion 454, the temperature of the heat exchange fluid is controlled by water baths 456 and 458. The etched layer 422 is made from silicon and conducts heat across the first and second portions, creating a temperature gradient in the device 410 between the first and second portions.

A sensor 460 (such as a microscope or a camera) is configured to sense a material characteristic of material within each one of the cells. The sensor 460 may simultaneously capture the material characteristic of the material within all of the cells, or only some of the cells. In some embodiments, the device 410 and/or the sensor 460 can be moved relative to each other such that if only some of the cells can be sensed simultaneously, the relative displacement enables sensing across all of the cells. The sensor data from the sensory 460 is delivered to a computer 462 where the sensor data may be processed, logged and/or displayed.

A temperature calibration 470 module can be used to determine the temperature of the device at positions between the first and second portions. The module 470 includes a temperature calibration fluid contained within a reservoir 474, the temperature calibration fluid having known properties. A pump 472 urges the temperature calibration fluid through the inlet 414A of the device 410. A pressure transducer 476 monitors the pressure of the temperature calibration fluid prior to its introduction into the device. The sensor 460 senses the material characteristics of the temperature calibration fluid, thereby determining the temperature therein. In some embodiments, the device 410 comprises a temperature calibration channel for receiving a temperature calibration fluid for monitoring the temperature of the device. In some embodiments, the temperature calibration fluid is flowed through the temperature calibration channel while a method according to the present invention is performed. In some embodiments, the temperature modulator 450 is applying stimulus to the device 410 and the temperature calibration fluid is flowed through the device 410 prior to the introduction of the sample fluid to determine the temperature at various locations of the device 410. Thermocouples (not shown) can be attached directly to the device 410 to measure temperature.

The pressure data from transducers 446, 448 and 476 are delivered to a computer 464 where the pressure data may be processed, logged, and/or displayed. In some embodiments, the computer 462 and 464 are the same computer.

Example 1—Direct Measurement of Fluid Phase Diagram

Figure 7A:
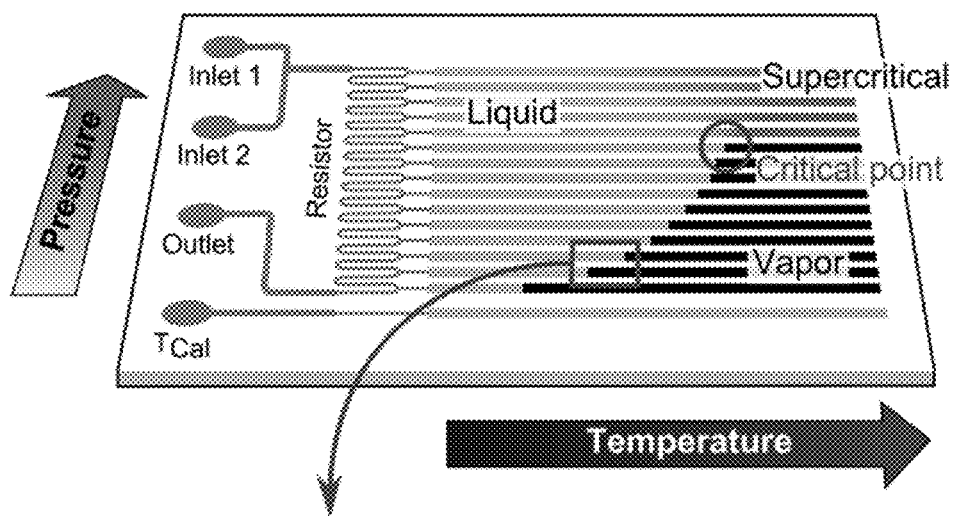
FIG. 7A is a schematic diagram of a microfluidic fluid phase-mapping device according to an embodiment of the invention, the device being arranged as a 2D array of cells subject to a vertical pressure gradient and a horizontal temperature gradient.
Figure 7B:
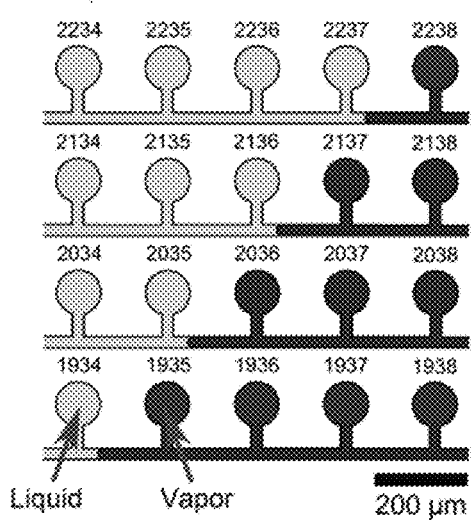
FIG. 7B is an illustration of enlarged view of certain cells according to the embodiment of the device of FIG. 7A.

A direct measurement of the full fluid phase diagram is performed, where a fluid's physical state is observed within 10,000 individual micro-wells simultaneously, each at a distinct pressure and temperature. Micro-wells are positioned in a square grid, where orthogonal, linear, pressure and temperature gradients are applied (FIGS. 7A and 7B). The phase-mapping device is made of glass-silicon to enable high pressures and temperatures, and the high thermal conductivity of the silicon (k·149 W·m$^{-1}$·K$^{-1}$) ensures local control of temperature. Both pure $CO_2$ and a 95% $CO_2$+5% $N_2$ mixture are tested, and the results are validated using NIST reference values. The critical pressures are determined to be within 1.2% of expected values. As opposed to traditional methods that require several days to complete, the phase-mapping device exploits short length-scales and generates the full phase diagram quickly within a single run.

The device was first characterized using pure $CO_2$. A linear pressure gradient ($P_{low}$=5.5 MPa to $P_{high}$=8.0 MPa) was distributed across the network by maintaining a continuous vertical single-phase liquid flow through a serpentine resistor channel. The resistor channel cross-section area (A=25 μm×25 μm) was low enough to (i) provide an elevated hydraulic resistance to render out-of-chip resistances negligible, (ii) ensure a manageable flow rate (Q=0.08 ml/min), and (iii) a low Reynold's number (Re=520). One hundred dead-end channels were positioned at intervals of 250 μm, and run horizontally across the chip from the resistor channel. Each horizontal channel has one hundred orthogonally connected micro-wells (diameter d=100 μm) at 200 μm intervals (FIG. 7B), to allow direct observation of phase properties without magnification. Under normal operation, the pressure distributes linearly along liquid phase in the resistor channel (vertically), effectively assigning each horizontal channel (and all 100 corresponding micro-wells) an identical pressure. A temperature gradient ($T_{low}$=13.7° C. to $T_{high}$=37.8° C.) was applied horizontally using external cooler and heater blocks.

Figures 8A, 8B:
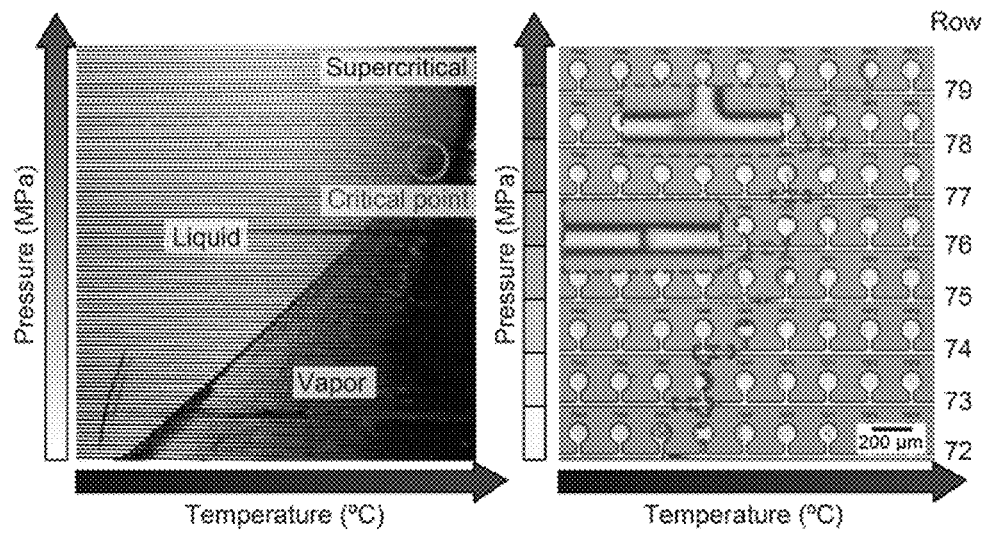
FIG. 8A is photograph taken by a consumer camera according to an embodiment of the device during a phase-mapping operation, where liquid, vapour, and supercritical regions are illustrated on the photograph.
FIG. 8B is a photograph taken by a microscope of the device according to the embodiment of FIG. 8A and having inset images showing enlarged views of liquid-vapor interfaces at various conditions.
Figure 8C:
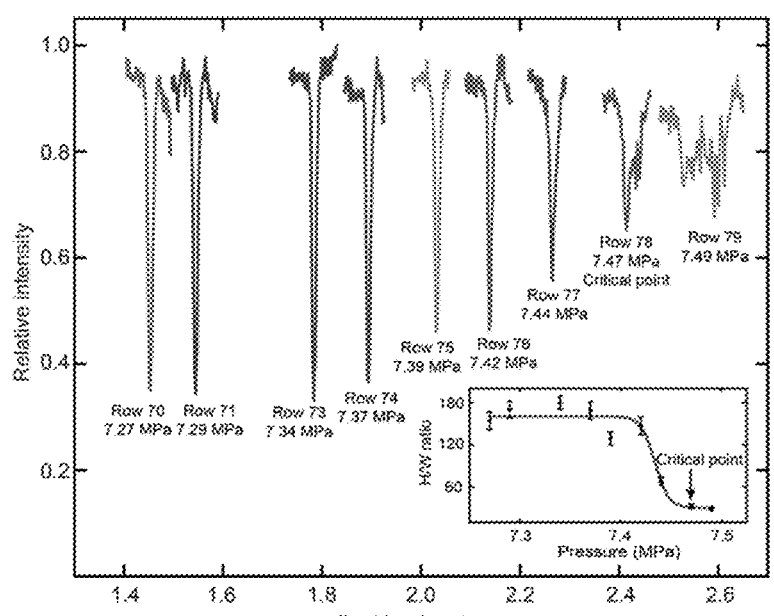
FIG. 8C is a chart illustrating a pixel intensity profile generated by image analysis across corresponding liquid-vapour interfaces having an inset showing how the height-to-width ratio of the pulses changes near the critical point.

FIG. 8A is a consumer camera image (image size~1"×1") of the chip in operation for a preliminary run, which shows how the liquid, vapor and supercritical states are clearly distinguishable by eye. A liquid-vapor saturation line traverses the chip, and becomes increasingly blurred as it nears the critical point. For precise phase mapping, a separate run was performed where a microscope was used to identify micro-wells nearest the liquid-vapor interface position. FIG. 8B shows a microscope image of an area containing the critical point. The distinct liquid-vapor interface vanishes at Row 78. In FIG. 8C, intensity profiles across the liquid-vapor interfaces are plotted for pressures approaching the critical point. A sharp pulse corresponds to sharp light-dark-light liquid-vapor transitions. Broader, shallower pulses are produced nearer the critical point. Through Gaussian fitting, the height and width of these pulses were extracted. The height-to-width ratio, an expression of peak quality, is plotted in the inset of FIG. 8C as a function of position along the horizontal channels, and fitted to a sigmoidal curve. This method of evaluating liquid-vapor interface quality provides a quantified method of establishing the critical point value, without relying on subjective operator assessment—typical of traditional methods. Here, critical point was measured at 7.47±0.07 MPa/31.7±0.5° C., which compares favorably to the NIST reported value of 7.38 MPa/31.1° C.—a 1.2% deviation in critical pressure.

Figure 8D:
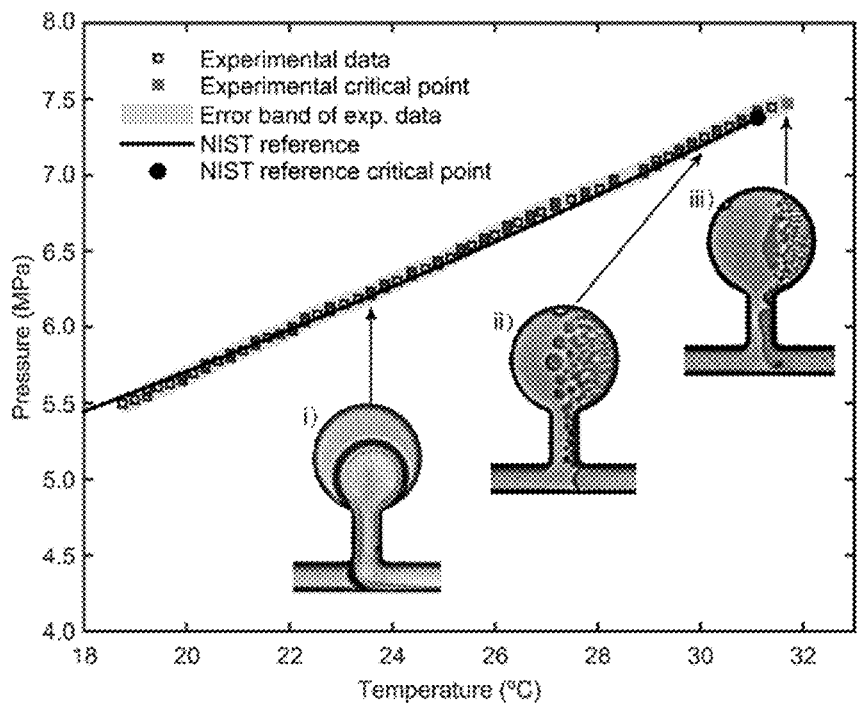
FIG. 8D is a chart illustrating pressure-temperature phase transition point measurements and validation with NIST reference points having inset images (contrast-enhanced, outside area removed) showing typical fluid behavior within micro-wells at various pressure-temperature conditions.

To compile the full phase diagram, the position of all liquid-vapor interfaces (for all horizontal channels) was measured. FIG. 8D shows the measured saturation line and critical point plotted with the NIST reference data. For all phase transition measurements, the standard deviation between the measured and NIST values was 0.03 MPa. The maximum pressure difference with respect to NIST reference data was −0.07 MPa. Similarly for temperature, the standard deviation was 0.2° C. and the maximum temperature difference was 0.5° C. The estimated error band based on the pressure (pump) and temperature (heater/chiller) uncertainties was ±0.07 MPa and ±0.5° C., and all NIST data fall within this range. With regard to resolution, the discretization of the field into micro-wells corresponds to 0.025 MPa and 0.24° C. per micro-well in this test. Reducing both the temperature and pressure range across the chip would improve accuracy and resolution—effectively zooming in to a narrower range. The accuracy achieved for even the relatively large P-T range here (FIG. 8A-D) is on par with existing technologies, such as PVT cells.

While each micro-well could be considered a single "point" on the P-T phase diagram, there is in fact a small temperature gradient of 0.14° C. within each well, providing additional information on phase kinetics. FIG. 8D shows three microscope images of micro-wells taken along the saturation line. The surface tension of $CO_2$ changes significantly from $P_{10}$, to the critical point, decreasing from 1.3 mN/m to zero. This marked difference in surface tension results in distinct bubbling kinetics at the interface at various pressures. At lower pressures and temperatures, a high interfacial tension prevents the formation of bubbles—only a single liquid-vapor interface is observed (sharp, well-defined meniscus shown in FIG. 8D, inset i). At higher pressures and temperatures, interfacial tension decreases and rapid bubbling was observed—biased to the high-temperature right-hand side of the micro-well (FIG. 8D, insets ii and iii). When the liquid-vapor interface in the horizontal channel was directly below a micro-well, nucleation (boiling) occurred on the right "hot" sidewall, with bubbles growing and flowing out of the well before collapsing at a position directly above the interface. This sidewall boiling mechanism is inherent to micro-wells nearer the critical point, where interfacial tension—a barrier to bubble formation—is low.

Figure 9:
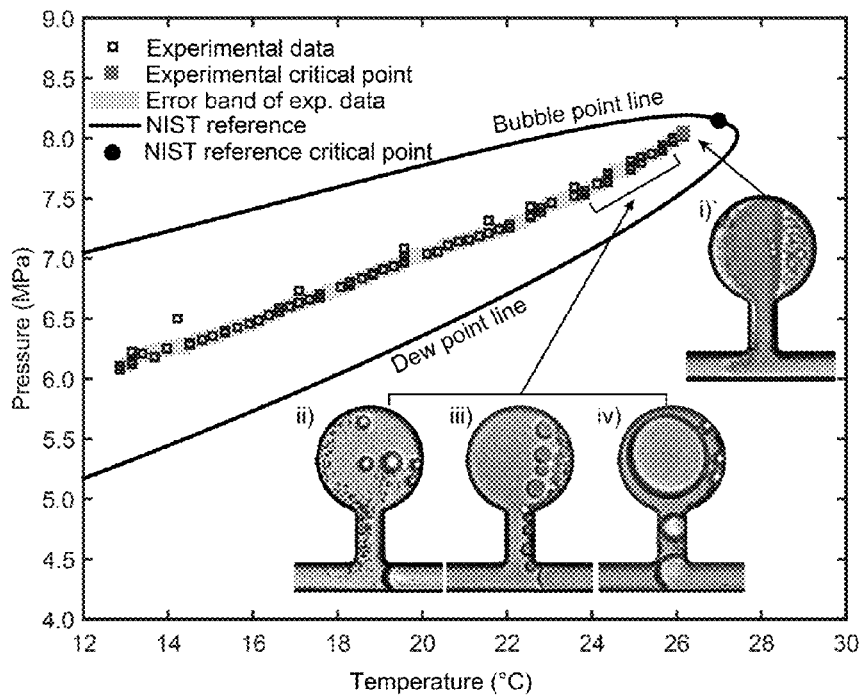
FIG. 9 is a chart illustrating the measurement of the fluid phase diagram of a 95% CO2+5% N2 mixture and comparison to NIST reference having inset images (contrast enhanced, outside area removed) showing typical fluid behavior within micro-wells at various P-T conditions.

To demonstrate the applicability of our phase-mapping device to mixtures, the phase diagram of a binary 95% $CO_2$+5% $N_2$ mixture was measured. For this experiment, pressures were set at 8.5 MPa and 6.0 MPa for the inlet and outlet, respectively, and the temperature gradient was the same as for the pure $CO_2$ experiment. In contrast to pure substances that are characterized by a single saturation line, the phase diagram of a fluid mixture is characterized by a phase envelope, bounded by an upper bubble point line and a lower dew point line. Within this envelope, both liquid and gas phases coexist in varying proportions. FIG. 9 shows the measured pressure-temperature diagram for the mixture, with the expected phase envelope (solid line—NIST reference). The single liquid-vapor saturation line observed was centered between the dew point line and bubble point line of the NIST reference (FIG. 9). This effective averaging is due to the interconnected nature of the micro-wells, and equilibration to a global state reminiscent of the fractional distillation process. Specifically, the lighter component ($N_2$) vaporizes first and preferentially accumulates on the right end of horizontal channels, resulting in a single effective liquid-vapor saturation line leading to the critical point. Near the critical point, intense bubbling behavior is observed as shown inset in FIG. 9. At the region just below critical point, several unique bubbling phenomena were observed at the interface (See FIG. 9 insets i, ii, iii, and iv). While a traditional phase envelope was not produced, the system nonetheless led to highly accurate critical point measurement: 8.05±0.07 MPa/26.2±0.5° C. and compares favorably to the NIST reference critical point, 8.15 MPa/27.0° C. predicted for this mixture—a 1.2% difference in critical pressure.

Notably, the addition of 5% $N_2$ to the $CO_2$ sample caused a 10% increase in the critical point pressure, and the device was shown fully capable of measuring each of these critical pressures at 1.2% error with respect to NIST reference values. The ability of the phase-mapping device to correctly measure critical point over a wide range underscores the importance and effectiveness of the method at measuring the critical point.

Regarding fundamental measurement time, two metrics are noteworthy, (i) equilibrium time and (ii) degree of multiplexing. The phase-mapping device has 10,000 micro-wells operating in parallel ($2\times10^{-4}$ μL per micro-well, or 2 μL for the entire array) that equilibrate in seconds. The phase-mapping device required ~20 s to re-equilibrate after a 0.1 MPa pressure change. In practice, the experiment with 10,000 micro-well data points described in FIG. 8D required 3 h to complete, including 1 h of preparation, 1 h of test, 1 h of temperature calibration and post-processing. In contrast, a traditional PVT system typically takes 8 to 10 h for a single P-T data point. A minimum of 800 hours (100 P-T data points) would be needed using a traditional PVT system to achieve similar resolution—an over 100-fold longer measurement time.

Example 2—Direct Measurement of Fluid Phase Diagram Using Interference Material

Another embodiment of the device is used. This embodiment leverages a secondary "non-participating" liquid piston isolation scheme (FIG. 5), which has enabled measurement of the phase envelope (including the critical point) of mixtures, for complete phase pressure-temperature analysis of mixtures. This isolation of micro-PVT cells expands the applicability to additional industrial processes.

The channel configuration for this new design is similar to the device of Example 1, with a series of perpendicular dead-end microchannels protruding at 90 degrees from a vertical microchannel. These 20 dead-end microchannels each support a series of 50 micro-PVT cells. First, test fluid is loaded into the device (as a gas), and then an inert, non-participating fluid, such as ethylene glycol, is flowed into the device to encase pockets of test fluid within each of the micro-wells. By applying a pressure difference between inlet 1 and the outlet 2 (inlet 2 is sealed), the ethylene glycol flows such as to create a linear pressure gradient, which effectively applies a fixed pressure to each horizontal channel (as a liquid piston). A temperature gradient is applied horizontally across the chip. As a result of local micro-PVT cell conditions, each independent pocket of test fluid will experience rapid phase change, resulting in a global map of phase properties, including gas-liquid ratios within the phase envelope. A temperature gradient (22.8° C.-87.4° C.) is applied perpendicular to the pressure gradient (0.6 MPa-8.7 MPa), enabling full mapping of the phase diagram of a test fluid. The full device houses 1,000 cells, not 50 as illustrated, and uses an interdigitated micro-cell design to maximize space efficiency. The experimental setup used to control the device is shown in FIG. 4.

Figure 10A:
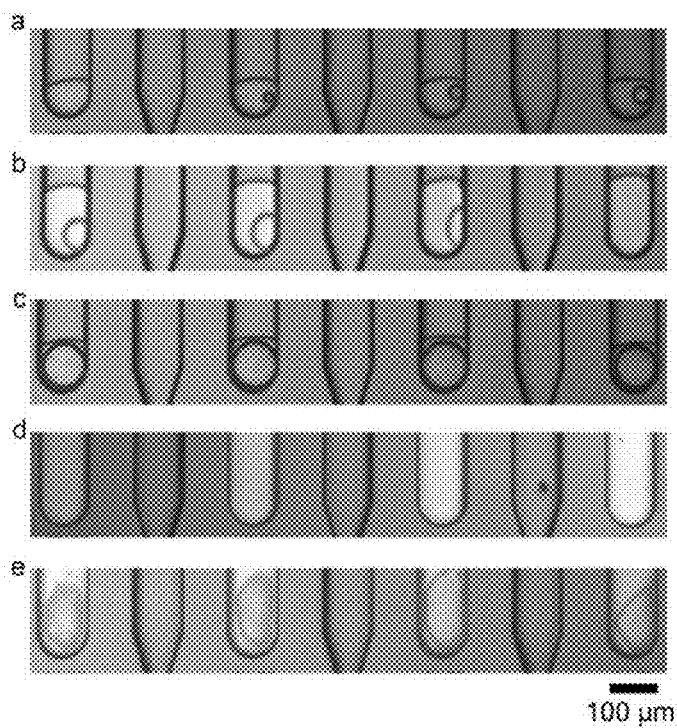
FIG. 10A is a photograph taken by a microscope illustrating various PVT cell phase configurations under different pressures and temperatures according to an embodiment where the cells are interdigitated and bottom portions of cells are shown, and where only the 1st, 3rd, 5th, and 7th pictured wells in each image are being discussed as they are disposed at the same pressure.
Figure 10B:
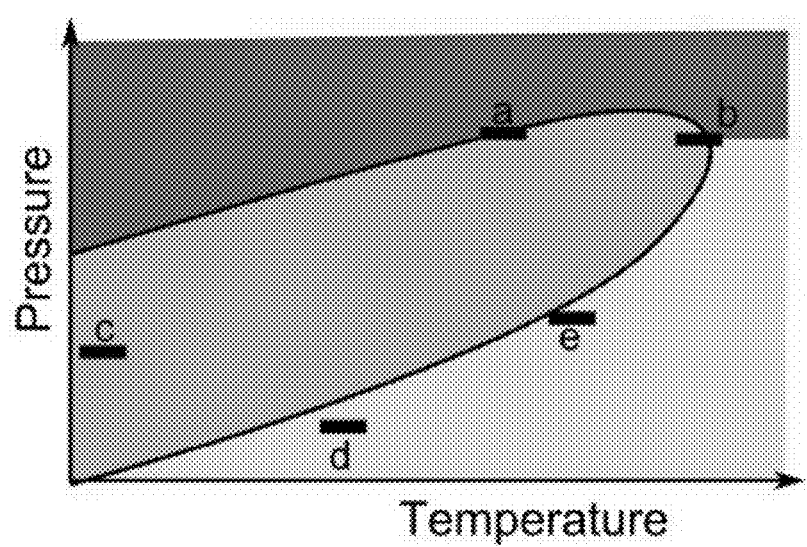
FIG. 10B is a chart illustrating the conditions at which each one of the series are disposed on a phase diagram.

Images representative of distinct regions of interest are highlighted in FIGS. 10A & 10B. In FIGS. 10A&B, at series "a" there is a two-phase region consisting largely of liquid, with small methane/propane bubbles beginning to appear, and becoming larger toward the right (higher temperature). Given the large proportion of liquid, the ethylene glycol "liquid piston" is almost fully extended in this region, and confines the methane/propane to the very tip of the PVT cells. In FIGS. 10A&B, at series "b" at higher temperatures, these methane/propane bubbles are larger, and the interface between these bubbles and the neighboring liquid disappears, which indicates the critical point and transition to the supercritical phase region. In FIGS. 10A&B, at series "c" the pressure is lower than in series "a", which results in larger bubble sizes. In FIGS. 10A&B, at series "d" at high temperature and low pressure, the methane/propane is fully vapor, and the pistons only extend roughly ⅔ of the length of the chambers. In FIGS. 10A&B, at series "e" the temperature and pressure is higher relative to series "d", and small liquid methane/propane films begin to appear.

Figure 11:
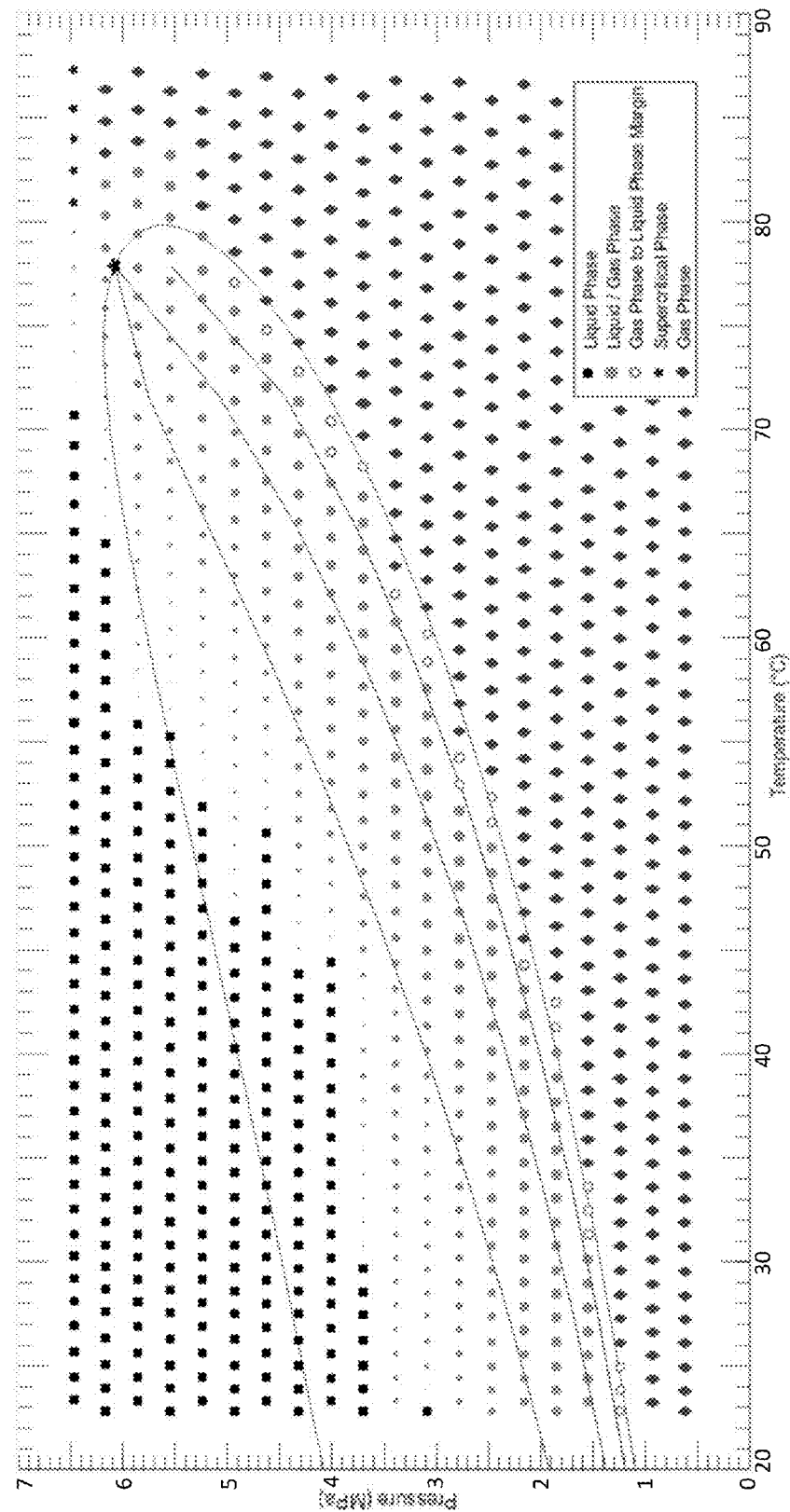
FIG. 11 is a chart illustrating observed conditions of a sample material in a phase diagram mapping operation where the material characteristic information sensed by the device is shown at various conditions and the NIST information for the material is illustrated by the curves, where the size of the circles denote the gas-vapour ratio and where the large star denotes the critical point predicted by a NIST-based model.

FIG. 11 shows how the measured phase envelope matches well with the expected phase diagram for a 20% propane/80% methane mixture (mole fraction). The phase boundary largely follows the NIST-predicted outline, with larger discrepancies at the top (bubble point line). The temperature gradient (22.8° C.-87.4° C.) and pressure gradient (0.6 MPa-8.7 MPa) were chosen such as to encompass a large region of the pressure-temperature, however, to obtain even more accurate resolution (for example, more precise critical point measurement). These gradients could be reduced to "zoom-in" on specific regions of the diagram.

Although a few example embodiments have been described in detail above, modifications are possible in the example embodiments without materially departing from embodiments disclosed herein. Accordingly, all such modifications are intended to be included within the scope of this disclosure.

What is claimed is:

1. A method for determining a material characteristic of a sample material comprising:
    loading a sample material to a plurality of cells;
    disposing an interference material relative to the sample material such that the interference material at least retards the transport of the sample material from a one of the cells to at least another one of the cells; and
    for each one of the cells, independently:
        applying a stimulus to the sample material in the cell such that a conditioned sample material is obtained; and
        sensing a material characteristic of the conditioned sample material.

2. The method of claim 1, wherein the applying the stimulus modulates pressure, temperature, voltage, radiation dose, electric field, magnetic field, or a combination thereof of the sample material in the cell.

3. The method of claim 2, wherein the applying the stimulus modulates the pressure of the sample material in the cell.

4. The method of claim 2, wherein the applying the stimulus comprises pressurizing the interference material, wherein the interference material communicates pressure to the cell thereby modulating the pressure of the sample material in the cell.

5. The method of claim 2, wherein the applying the stimulus modulates temperature of the sample material in the cell.

6. The method of claim 5, wherein the temperature is modulated by a heat exchanger.

7. The method of claim 6, wherein at least a portion of the heat exchanger is integral with at least a portion of the cell.

8. The method of claim 2, wherein the plurality of cells comprises a plurality of rows and a plurality of columns, the stimulus modulates a first material property selected from pressure, temperature, voltage, radiation dose, electric field, and magnetic field parameter such that the first material property is substantially constant in cells of a row of the plurality of rows, and wherein the stimulus modulates a second material property selected from pressure, temperature, voltage, radiation dose, electric field, and magnetic field parameter such that the second material property is substantially constant in cells of a column of the plurality of columns.

9. The method of claim 1, wherein the transport being retarded includes transport across an interface between the sample material and the interference material.

10. The method of claim 1, further comprising determining a critical point, a dew point, a bubble point, a melting point, a boiling point, a eutectic point, a cricondentherm, a cricondenbar, quality lines, or a combination thereof using the sensed material characteristic.

11. A method for determining a material characteristic of a material comprising:
    flowing a material through a main channel such that a first pressure is established and is communicated to a branch channel from the main channel;
    applying a first stimulus to material within a first space of the branch channel for modulating a material property parameter of the material within the first space of the branch channel;
    applying a second stimulus to material within a second space of the branch channel for modulating a material property parameter of the material within the second space of the branch channel;
    sensing a material characteristic of the material within the first space of the branch channel; and
    sensing a material characteristic of the material within the second space of the branch channel.

12. The method of claim 11, wherein the material property parameter of the material within the first space of the branch channel, and the material property parameter of the material within the second space of the branch channel are, independently, temperature.

13. The method of claim 11, wherein the flowing of the material through the main channel establishes a second pressure downstream from the first pressure, and wherein the second pressure is communicated to a downstream branch channel, the downstream branch channel connecting to the main channel downstream of the branch channel;
    wherein the method further comprises:
        applying a third stimulus to material within a first space of the downstream branch channel for modulating a material property parameter of the material within the first space of the downstream branch channel;
        applying a fourth stimulus to material within a second space of the downstream branch channel for modulating a material property parameter of the material within the second space of the downstream branch channel;
        sensing a material characteristic of the material within the first space of the downstream branch channel; and
        sensing a material characteristic of the material within the second space of the downstream branch channel.

14. The method of claim 13, wherein the branch channel and the downstream branch channel are substantially parallel, wherein the distance from the connection point of the main channel and the branch channel to the first space of the branch channel is about equal to the distance from the connection point of the main channel and the downstream branch channel to the first space of the downstream branch channel, and wherein the modulated material property of the material within the first space of the branch channel is modulated to a substantially equal condition to the modulated material property of the material within the first space of the downstream branch channel.

15. The method of claim 11, wherein the branch channel comprises a first cell and a second cell, the first space of the branch channel being defined by the first cell, the second space of the branch channel being defined by the second cell,
    wherein the material within the first space of the branch channel is a first sample fluid, and the material within the second space of the branch channel is a second sample fluid; and
    wherein the flowed material is an interference material that at least retards the transport of the first sample fluid from the first space of the branch channel to the second space of the branch channel, and at least retards the transport of the second sample fluid from the second space of the branch channel to the first space of the branch channel.

16. An apparatus for determining phase properties of a sample material comprising:
    a fluid device comprising:
        a plurality of cells;
        a channel connected to the plurality of cells, the channel configured receive a flow of an interference material such that the interference material at least retards the transport of a sample material disposed one of the cells to another of the cells;
    a stimulator configured to apply an individual stimulus to each one of the cells to condition sample material disposed therein; and
    a sensor configured to sense a material characteristic of material within each one of the cells.

17. The apparatus of claim 16, wherein the stimulator comprises a pressure modulator for modulating the pressure of material within each one of the cells.

18. The apparatus of claim 16, wherein the channel comprises a main channel and at least one branch channel connected to the main channel configured such that, when the interference material is pumped through the main channel, the pressure in each branch channel, independently, is substantially the same.

19. The apparatus of claim 16, wherein the device comprises an sensory layer and an etched layer, wherein the volumes of the channel and the volumes of the plurality of walls are defined by void space between the sensory layer and the etched layer.

20. The apparatus of claim 16, wherein the stimulator comprises a temperature modulator for modulating the temperature of the sample material within each cell of the plurality of cells.

\* \* \* \* \*